United States Patent
Kawanaka et al.

(10) Patent No.: US 9,970,850 B2
(45) Date of Patent: May 15, 2018

(54) SHEET OF COLLOIDAL CRYSTALS IMMOBILIZED IN RESIN, METHOD OF DISPLAYING STRUCTURAL COLOR USING SAME, METHOD FOR DETECTING UNEVENNESS DISTRIBUTION OR HARDNESS DISTRIBUTION OF SUBJECT USING SAME, AND STRUCTURAL COLOR SHEET

(71) Applicants: Fuji Kagaku Corporation, Osaka (JP); National Institute For Materials Science, Ibarki (JP)

(72) Inventors: Satoshi Kawanaka, Osaka (JP); Fumio Uchida, Osaka (JP); Tsutomu Sawada, Ibaraki (JP); Seiichi Furumi, Ibaraki (JP); Hiroshi Fudoji, Ibaraki (JP)

(73) Assignees: NATIONAL INSTITUTE FOR MATERIALS SCIENCE, Ibaraki (JP); FUJI KAGAKU CORPORATION, Osaka (JP)

( * ) Notice: Subject to any disclaimer, the term of this patent is extended or adjusted under 35 U.S.C. 154(b) by 0 days. days.

(21) Appl. No.: 14/910,445

(22) PCT Filed: Aug. 5, 2014

(86) PCT No.: PCT/JP2014/070653
§ 371 (c)(1),
(2) Date: Feb. 5, 2016

(87) PCT Pub. No.: WO2015/020067
PCT Pub. Date: Feb. 12, 2015

(65) Prior Publication Data
US 2016/0178493 A1   Jun. 23, 2016

(30) Foreign Application Priority Data

Aug. 6, 2013  (JP) .................................. 2013-163657
Mar. 10, 2014  (JP) .................................. 2014-046967

(51) Int. Cl.
*G01B 11/24*  (2006.01)
*G01N 3/06*   (2006.01)
(Continued)

(52) U.S. Cl.
CPC ........... *G01N 3/068* (2013.01); *G01B 11/306* (2013.01); *G02B 1/005* (2013.01); *G02B 1/04* (2013.01);
(Continued)

(58) Field of Classification Search
CPC ........ G01B 11/306; G02B 1/005; G02B 1/04; G02B 5/1861; G02B 5/206; B82Y 20/00; G02F 1/3511; B01J 13/00; G01N 21/01
(Continued)

(56) References Cited

U.S. PATENT DOCUMENTS 4,632,517 A * 12/1986 Asher .................. G01J 3/12
                                                356/303
5,139,611 A   8/1992 Pusey et al.
(Continued)

FOREIGN PATENT DOCUMENTS

JP    3-504462       3/1991
JP    2002028471 A   1/2002
(Continued)

OTHER PUBLICATIONS

International Search Report, PCT/JP2014/070653 dated Nov. 11, 2014 (2 pages).
(Continued)

*Primary Examiner* — Isiaka Akanbi
(74) *Attorney, Agent, or Firm* — Eversheds Sutherland (US) LLP

(57) ABSTRACT

A sheet of colloidal crystals immobilized in resin exhibiting intense structural color and allowing easy observation thereof from squarely facing direction against the surface;
(Continued)

and application thereof are provided. The sheet includes crystal domains comprising colloidal crystals immobilized in resin. The Bragg reflection intensity resulting from crystal domains according to back reflection spectrum measurement to the sheet surface satisfies the following conditions (1) and (2). (1) When elevation angle from the sheet surface is in a range of at least 60° and less than 90° and measurement is performed at a predetermined azimuth angle on the sheet surface, intensity is not 0 and (2) when elevation angle from the sheet surface is in the range of at least 60° and less than 90° and azimuth dependency on the sheet surface is measured, the intensity exhibits a maximum value at the predetermined azimuth angle.

20 Claims, 17 Drawing Sheets

(51) Int. Cl.
*G02B 1/04* (2006.01)
*G02B 1/00* (2006.01)
*G02B 5/20* (2006.01)
*G02B 5/26* (2006.01)
*G01B 11/30* (2006.01)
*G02B 5/18* (2006.01)

(52) U.S. Cl.
CPC ........... *G02B 5/1861* (2013.01); *G02B 5/206* (2013.01); *G02B 5/26* (2013.01)

(58) Field of Classification Search
USPC .................................................. 356/601–624
See application file for complete search history.

(56) References Cited

U.S. PATENT DOCUMENTS

| | | | | |
|---|---|---|---|---|
| 5,281,370 A | * | 1/1994 | Asher | B82Y 20/00 264/1.1 |
| 5,452,123 A | * | 9/1995 | Asher | B82Y 20/00 359/296 |
| 5,944,994 A | * | 8/1999 | Asher | B82Y 20/00 106/3 |
| 6,894,086 B2 | * | 5/2005 | Munro | C09D 5/004 264/1.7 |
| 7,045,195 B2 | | 5/2006 | Ozin et al. | |
| 8,252,412 B2 | * | 8/2012 | Purdy | G02B 1/005 359/588 |
| 8,440,294 B2 | * | 5/2013 | Hara | G02B 5/203 356/121 |
| 2004/0246413 A1 | * | 12/2004 | Stephenson | C09D 5/24 349/113 |

FOREIGN PATENT DOCUMENTS

| | | |
|---|---|---|
| JP | 2010155068 A | 7/2010 |
| JP | 2012000994 A | 1/2012 |
| JP | 2012210311 A | 11/2012 |

OTHER PUBLICATIONS

Iwayama, Yumie et al., "Optically Tunable Gelled Photonoic Crystal Covering Almost the Entire Visible Light Wavelength Region", Langmuir, The ACS Journal of Surfaces and Colloids, vol. 19, No. 4, Feb. 18, 2003 (4 pgs.).

Fudouzi, Hiroshi et al., "Colloidal Crystals with Tunable Colors and Their Use as Photonic Papers", Langmuir 2003, vol. 19, pp. 9653-9660.

* cited by examiner

SHEET OF COLLOIDAL CRYSTALS IMMOBILIZED IN RESIN, METHOD OF DISPLAYING STRUCTURAL COLOR USING SAME, METHOD FOR DETECTING UNEVENNESS DISTRIBUTION OR HARDNESS DISTRIBUTION OF SUBJECT USING SAME, AND STRUCTURAL COLOR SHEET

CROSS-REFERENCE TO RELATED APPLICATIONS

This application claims priority to Japanese Application 2013-163657 filed Aug. 6, 2013; Japanese Application No. 2014-046967 filed Mar. 10, 2014; and International Patent Application PCT/JP2014/070653 filed Aug. 5, 2014, the subject matter of which is expressly incorporated herein by reference in its entirety.

TECHNICAL FIELD

The present invention relates to a sheet of colloidal crystals immobilized in resin and an application utilizing the same. Specifically, the present invention relates to the sheet of colloidal crystals immobilized in resin capable of making its structural color developed strongly in the coloration and observed easily even from a squarely facing direction and relates to applications thereof.

BACKGROUND ART

The matter with inner structure in which fine particles of a uniform particle size (particle diameter: 50 nm to 1000 nm, which is called a colloidal particle) are arranged in a three-dimensional periodic manner is called a colloidal crystal. The colloidal crystal appears with coloration by the effect of Bragg reflection of light due to the periodic structure such that it is expected to become a material expressing coloration (structural color) caused by the structure (i.e., material of structural color) wherein the coloration by structure is different from coloration by dye. And a colloidal crystal where resin is filled in space between fine particles is also known (it is also called colloidal crystals immobilized in resin).

In such colloidal crystals, there is a colloidal crystal of polycrystal-like state in which crystal domains of from a micron size to a millimeter size in which particles are arranged in a three dimensional periodic arrangement are put together with a randomly orientated relationship with each other (for example, Non-patent Reference 1). In such a colloidal crystal of polycrystal-like state, condition of angles which gives rise to Bragg reflection differs in each crystal domain such that, as a whole, the structural coloration effect may be obtained in an arbitrary direction. This crystal domain is generally defined as an area constituted of a single crystal.

In another colloidal crystal, there may be obtained a state that crystal domains having sizes not exceeding several millimeters are oriented such that specific crystal lattice planes are orderly arranged in a specific space orientation in the crystal domains. As a manufacturing method of such a colloidal crystal, for example, it is named to produce a colloidal crystal by oscillating relatively parallel planes opposing each other after inserting a predetermined colloidal solution in a narrow gap between the parallel planes wherein the amplitude of the oscillation is set comparable to the gap of the two planes (for example, Patent Reference 1).

There is a colloidal crystal sheet in which colloidal crystals oriented in such a way are immobilized by elastic member such as polydimethyl silicone (hereinafter, called "oriented colloidal crystal sheet") (for example, refer to Non-patent Reference 2). In the oriented colloidal crystal sheet, since the angle condition to cause the Bragg reflection by a specific crystal lattice plane is to be the same as that in any of the crystal domains, a strong effect of the structural coloration can be obtained in the specific direction.

However, the colloidal crystal of polycrystal-like state has a disadvantage that the intensity of coloration is weak since the number of crystal domains that contribute to the Bragg reflection to an arbitrary direction is less than the number of crystal domains that contribute to the Bragg reflection to a specific space orientation in the oriented colloidal crystal sheet (for example, a colloidal crystal sheet in Non-patent Reference 2).

Further, in a colloidal crystal of Patent Reference 1 and an oriented colloidal crystal sheet of Non-patent Reference 2, since the crystal domains are oriented such that the specific crystal lattice plane may be arranged to be parallel to the surface of the sheet, if the effect of the structural coloration caused by the Bragg reflection is supposed to be given to an observer who intends to make an observation from the squarely facing direction (i.e., a direction perpendicular to the surface) against the surface of the colloidal crystal and the colloidal crystal sheet, it is necessary to irradiate the surface from the squarely facing direction with the illumination light such that the illumination axis and the observation axis overlap. The above-mentioned configuration is not so practical that it is desired to improve the colloidal crystal.

Therefore, there is a demand to develop a colloidal crystal to achieve the structural coloration effect strongly in the squarely facing direction against the surface of the colloidal crystal wherein the squarely facing direction is the observation direction most naturally selected.

PRIOR ART REFERENCES

Patent References

[Patent Reference 1] Japanese Patent Application Publication No. H3(1991)-504462
[Non-Patent Reference 1] Iwayama et al., Langmuir 19 (2003) 977-980
[Non-Patent Reference 2] Fudouzi, Xia, Langmuir 19 (2003) 9653-9660

SUMMARY OF THE INVENTION

Problem to be Solved by the Invention

As mentioned above, the issue of the present invention is to provide a sheet of colloidal crystals immobilized in resin that exhibits intense structural color and may enable the structural color to be observed easily from a squarely facing direction against a surface; and an application thereof.

Means to Solve the Problem

A sheet of colloidal crystals immobilized in resin including a plurality of crystal domains in which colloidal particles are immobilized in resin according to the present invention is characterized in that, in back reflection spectrum measurement with respect to a sheet surface of the sheet of colloidal crystals immobilized in resin, intensity of Bragg reflection caused by the plurality of crystal domains satisfies as follows: (1) the intensity is not zero (0) if measured with respect to a predetermined azimuth angle on the sheet surface when an elevation angle from the sheet surface is in a range of at least 60 degree and less than 90 degree; and (2) the intensity exhibits the maximum in the predetermined azimuth angle if measured with respect to dependency of the azimuth angle on the sheet surface when the elevation angle from the sheet surface is in a range of at least 60 degree and less than 90 degree, whereby the above-mentioned problem is solved.

Here, the sheet of colloidal crystals immobilized in resin may signify what is like a sheet shape in which the above-mentioned plurality of crystal domains are immobilized in resin so as to maintain respective crystal states thereof. The shape of sheet-like form may be a shape which is typically interpreted as the sheet form, and may be, for example, a plate or a sheet shape having a certain thickness. In particular, it is preferable that flexibly elastic deformation and/or flexibly plastic deformation in the thickness direction is allowed for the sheet. In general, this colloidal crystal sheet exhibits a rectangle in the plan view.

This type of colloidal crystal sheet could be manufactured by a shearing treatment. The shearing treatment is may be such a treatment that surfaces of the sheet opposing each other (for example, the upper surface and the bottom surface) are moved with a relative displacement in one direction. This direction (shearing direction) may be in parallel or substantially parallel to the sheet surface. Also, it is preferable that the relative displacement is a single or multiple of reciprocating motions. The direction of the predetermined azimuth angle may be a direction perpendicular to the shearing direction of the shearing treatment. A state in which the intensity of the Bragg reflection caused in the plurality of crystal domains is not 0 may denote that light caused by the Bragg reflection is recognized beyond measurement errors. Specifically, it is a state in which a peak caused by the Bragg reflection is recognized in the reflection spectrum measurement. And the back reflection spectrum measurement with respect to the sheet surface in such a state may be conducted in the whole range of the elevation angle of at least 60 degree and less than 90 degree from the sheet surface. Alternatively, the measurement may be performed in part of the whole range. When the measurement is conducted with respect to a predetermined azimuth angle on the sheet surface, the measurement may be conducted at any azimuth angle including the predetermined azimuth angle.

The particle concentration of the colloidal particles may be not less than 2% by volume and not exceeding 35% by volume. More preferably, it may be not exceeding 25% by volume, and yet more preferably it may be not exceeding 20% by volume. On the other hand, if colloidal crystal formation is considered, the particle concentration may be more preferably at least 5% by volume, and yet more preferably it may be at least 10% by volume. The resin may be selected from the group consisting of acrylic resin, epoxy resin, siloxane resin (silicone), urethane resin, polyester resin, alkyd resin, fluororesin, and polyether resin.

The resin may be an acrylic resin, and a compound to form the acrylic resin is at least one selected from the group consisting of methyl (meth)acrylate, 2-hydroxyethyl (meth)acrylate, 2-hydroxypropyl (meth)acrylate, 4-hydroxybutyl (meth)acrylate, methoxy triethylene glycol (meth)acrylate, methoxy tetraethylene glycol (meth)acrylate, methoxy polyethylene glycol (meth)acrylate, ethylene di(meth)acrylate, triethylene glycol di(meth)acrylate, tetraethylene glycol di(meth)acrylate, polyethylene glycol di(meth)acrylate, polypropylene glycol di(meth)acrylate, trimethylolpropane tri(meth)acrylate, pentaerythritol tri(meth)acrylate, dipentaerythritol hexa(meth)acrylate, and pentaerythritol tetra(meth)acrylate.

The resin may be an epoxy resin, and a compound to form the epoxy resin may include a diglycidyl ester derivative compound and/or a diglycidyl ether derivative compound, and a phthalic anhydride derivative compound. The diglycidyl ester derivative compound may be phthalic acid diglycidyl ester and/or hexahydrophthalic acid diglycidyl ester. The diglycidyl ether derivative compound may be at least one selected from the group consisting of glycerol polyglycidyl ether, 1,4-butanediol diglycidyl ether, and bisphenol-A diglycidyl ether. The phthalic anhydride derivative compound may be 4-methylhexahydrophthalic anhydride and/or hexahydrophthalic anhydride. The sheet may have a thickness of more than 0.3 mm and not exceeding 10 mm. It may be more preferably at least 0.5 mm and yet more preferably at least 0.7 mm. On the other hand, if the easiness of manufacturing the sheet of colloidal crystals immobilized in resin is considered, the sheet thickness is more preferably not exceeding 5 mm and yet more preferably not exceeding 3 mm. Some of the plurality of crystal domains may have a crystal lattice plane which is inclined to the sheet surface and some of the plurality of crystal domains may have a crystal lattice plane oriented to the direction of the predetermined azimuth angle.

A method of displaying a structural color based on colloidal crystals according to the present invention includes the step of irradiating the sheet of colloidal crystals immobilized in resin with illumination light, whereby the above-mentioned problem is solved. In the step of irradiating the sheet with the illumination light, the sheet may be irradiated with the illumination light from a direction different from a direction squarely facing the sheet surface of the above-mentioned sheet of colloidal crystals immobilized in resin. The sheet of colloidal crystals immobilized in resin is manufactured by applying a shearing treatment and the step of irradiating the illumination light may comprise irradiating the illumination light from the direction orthogonal to the shearing direction of the shearing treatment. The sheet of colloidal crystals immobilized in resin may have a pattern comprising a character or a figure. The sheet of colloidal crystals immobilized in resin may be sandwiched at least between a hard transparent plate and a relief plate in which a pattern comprised of a character or a figure is formed in a concave and convex pattern, and there may be included the step of pressing the sheet of colloidal crystals immobilized in resin with the hard transparent plate prior to the step of irradiating the illumination light.

A method of detecting the unevenness distribution or the hardness distribution of a test object according to the present invention comprises the steps of: covering a test object with the sheet of colloidal crystals immobilized in resin and pressing the sheet with a hard transparent plate; irradiating illumination light on the sheet of colloidal crystals immobilized in resin and observing the sheet of colloidal crystals immobilized in resin through the hard transparent plate; and detecting the unevenness distribution or the hardness distribution based on observation results obtained in the observation step, whereby the above-mentioned problem is solved. In the observation step, the observation may be conducted by irradiating the illumination light from a direction different from a direction squarely facing the sheet surface of the sheet of colloidal crystals immobilized in resin. The detecting step may comprise, if the observation results are the same as those of the sheet of colloidal crystals immobilized in resin before the pressing step, detecting that the test object has no unevenness or hardness distribution, while, if the observation results are different from those of the sheet of colloidal crystals immobilized in resin before the pressing step, detecting that the test object has unevenness or hardness distribution.

With respect to a structural color sheet in which a plurality of sheet pieces of colloidal crystals immobilized in resin are immobilized in resin according to the present invention, the plurality of sheet pieces of colloidal crystals immobilized in resin comprises what is cut out of the above-mentioned sheet of colloidal crystals immobilized in resin and the plurality of sheet pieces of colloidal crystals immobilized in resin are positioned in an arbitrary orientation relationship in the resin, whereby the above-mentioned problem is solved.

Effects of the Invention

The sheet of colloidal crystals immobilized in resin according to the present invention includes a plurality of crystal domains in which colloidal particles are immobilized in resin and intensity of Bragg reflection caused in the plurality of crystal domains in the back reflection spectrum measurement to the sheet surface of the sheet of colloidal crystals immobilized in resin satisfies the following Conditions (1) and (2).

(1) The intensity of Bragg reflection is not zero (0) if measured with respect to a predetermined direction on the sheet surface and in a range of an elevation angle from the sheet surface of at least 60 degree and less than 90 degree; and (2) the intensity of the Bragg reflection exhibits the maximum at the predetermined azimuth direction if measured with respect to dependency of the azimuth angle on the sheet surface in the range of the elevation angle from the sheet surface of at least 60 degree and less than 90 degree.

Above-mentioned Condition (1) allows the Bragg reflection to be observed without overlapping of the illumination axis of illumination light and the observation axis of an observer who squarely faces the sheet surface of the sheet of colloidal crystals immobilized in resin according to the present invention, and therefore, allows the observer squarely facing the sheet surface to easily observe a structural color. Also above-mentioned Condition (2) allows the sheet of colloidal crystals immobilized in resin according to the present invention to cause the strong color development of the structural color. Furthermore, the use of the sheet of colloidal crystals immobilized in resin according to the present invention, the sheet satisfying the above-mentioned Conditions (1) and (2), allows the observer to observe the structural color under the condition that surface reflected light does not overlap Bragg reflected light, whereby the effect of clear color development is achieved.

The use of the sheet of colloidal crystals immobilized in resin according to the present invention makes it possible to display a structural color and detect the unevenness or hardness distribution of a test object. Furthermore, a structural color sheet including sheet pieces of colloidal crystals immobilized in resin that are cut out from the sheet of colloidal crystals immobilized in resin according to the present invention makes it possible to produce an effect of color development even with irradiation of illumination light from an arbitrary direction, and therefore, has an advantage that there is no limitation in practices.

EMBODIMENT FOR CARRYING OUT THE INVENTION

Figure 1A:
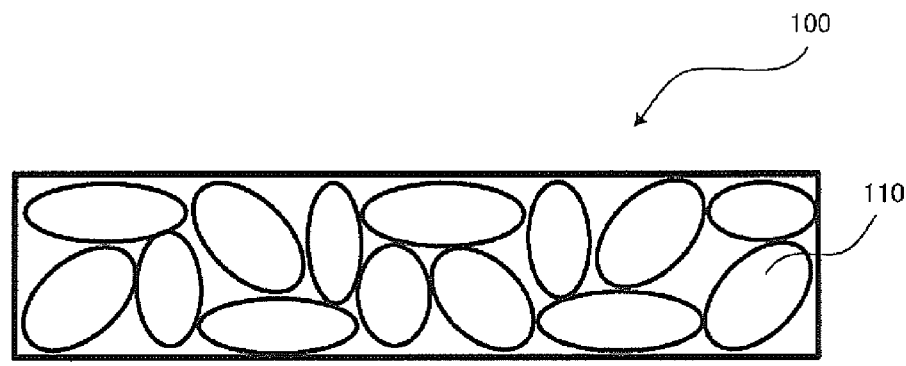
FIG. 1A is a schematic diagram illustrating a sheet of colloidal crystals immobilized in resin according to the present invention.

Hereinafter, with reference to the drawings, embodiments of the present invention will be described in detail. It should be noted that like reference numerals refer to like elements, and a description thereof will be omitted.

Embodiment 1

In Embodiment 1, a sheet of colloidal crystals immobilized in resin according to the present invention and a method of producing the same will be described in detail.

Figure 1B:
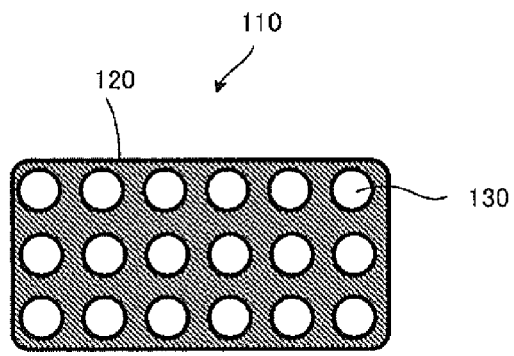
FIG. 1B is a schematic diagram illustrating crystal domains in the sheet of colloidal crystals immobilized in resin.

FIGS. 1A and 1B are schematic diagrams illustrating a sheet of colloidal crystals immobilized in resin according to the present invention. The sheet of colloidal crystals immobilized in resin 100 according to the present invention includes a plurality of crystal domains 110 (FIG. 1A). The plurality of crystal domains 110 comprise colloidal particles 130 immobilized in a resin 120 (FIG. 1B). Here, a three-dimensional periodic arrangement of the colloidal particles 130 in the plurality of crystal domains 110 is made so as to satisfy Bragg reflection conditions.

The resin 120 denotes a solid material formed of a polymer, such as synthetic resin, plastics, or elastomer. The resin 120 is formed of at least one kind of compound, and is a polymer made by the polymerization of a monomer, an oligomer, a macromer, or a combination of the at least one compound. Referring to a later-mentioned method of producing the sheet of colloidal crystals immobilized in resin 100 according to the present invention (FIG. 4), as long as a liquid colloidal dispersion containing at least one kind of compound to form the resin 120 is in a colloidal crystal state, the at least one kind of compound is applicable. The suitable selection of the kinds of compounds and blending thereof allow the resin to have a desired hardness or a desired flexibility under a usage environment. Here, the colloidal state denotes a state in which, typically, fine particles or macromolecules having a diameter of approximately 50 nm to 1000 nm ($5 \times 10^{-5}$ mm to $10^{-3}$ mm) are dispersed in a homogeneous medium, and a liquid in such a colloidal state may be called as a colloid liquid or a liquid colloidal dispersion. Furthermore, the colloidal crystal state may refer to a state in which such fine particles or macromolecules or the like are regularly arranged. It is considered that a liquid colloidal dispersion in such a colloidal crystal state is to constitute a crystal domain.

More specifically, the resin 120 may be selected from the group consisting of acrylic resin, epoxy resin, siloxane resin (silicone), urethane resin, polyester resin, alkyd resin, fluororesin, and polyether resin. These resins are capable of immobilizing colloidal particles so as to satisfy the above-mentioned Conditions (1) and (2). The resin 120 is preferably an acrylic resin or an epoxy resin. These resins make it possible to securely achieve the sheet of colloidal crystals immobilized in resin according to the present invention by the later-mentioned shearing treatment.

In the case where the resin 120 is an acrylic resin, examples of a compound to form the acrylic resin include monofunctional monomers, such as methyl (meth)acrylate, 2-hydroxyethyl (meth)acrylate, 2-hydroxypropyl (meth)acrylate, 4-hydroxybutyl (meth)acrylate, methoxy triethylene glycol (meth)acrylate, methoxy tetraethylene glycol (meth)acrylate, and methoxy polyethylene glycol (meth)acrylate; bifunctional monomers, such as ethylene di(meth)acrylate, triethylene glycol di(meth)acrylate, tetraethylene glycol di(meth)acrylate, polyethylene glycol di(meth)acrylate, and polypropylene glycol di(meth)acrylate; and polyfunctional monomers, such as trimethylolpropane tri(meth)acrylate, pentaerythritol tri(meth)acrylate, dipentaerythritol hexa(meth)acrylate, and pentaerythritol tetra(meth)acrylate, and these may be used alone or in combination of two or more kinds thereof. These are preferable because of their easy availability and simple handling.

In the case where the resin 120 is an epoxy resin, a compound to form the epoxy resin may include a diglycidyl ester derivative compound and/or a diglycidyl ether derivative compound as a base, and a phthalic anhydride derivative compound as a curing agent. More specifically, the diglycidyl ester derivative compound may be phthalic acid diglycidyl ester and/or hexahydrophthalic acid diglycidyl ester. The diglycidyl ether derivative compound may be at least one selected from the group consisting of glycerol polyglycidyl ether, 1,4-butanediol diglycidyl ether, and bisphenol-A diglycidyl ether. The phthalic anhydride derivative compound may be 4-methylhexahydrophthalic anhydride and/or hexahydrophthalic anhydride. These are preferable because of their easy availability and simple handling.

The hardness and flexibility of the resin 120 are sometimes changed depending on a resin selected, or temperature or the like in a usage environment, but, for example, in the case where the resin 120 does not easily become deformed under a usage environment, the sheet of colloidal crystals immobilized in resin is preferable because, for example, the sheet is available for decoration to stably display a certain color. For example, in the case where the resin 120 easily becomes deformed under a usage environment, the colloidal crystals immobilized in resin are preferable because they are available for pattern display that utilizes deformation of the resin, or for the detection of unevenness distribution or hardness distribution. A person skilled in the art can suitably select such resin 120 having a desired hardness or flexibility.

The colloidal particles 130, having a particle diameter of 50 nm to 1000 nm, are silica particles, polystyrene particles, polymer latex particles, oxide particles such as titanium dioxide, metal particles, or composite particles constituted of a combination of different materials, but are not limited to these. It should be noted that the composite particle is constituted of a combination of two or more kinds of different materials, and denotes what is formed as one particle by encapsulating one material in another material, or what is formed as one particle by binding hemispherical parts constituted of different materials, or the like. As mentioned above, the colloidal particles 130 are arranged in a three-dimensional periodic manner.

Figure 2A:
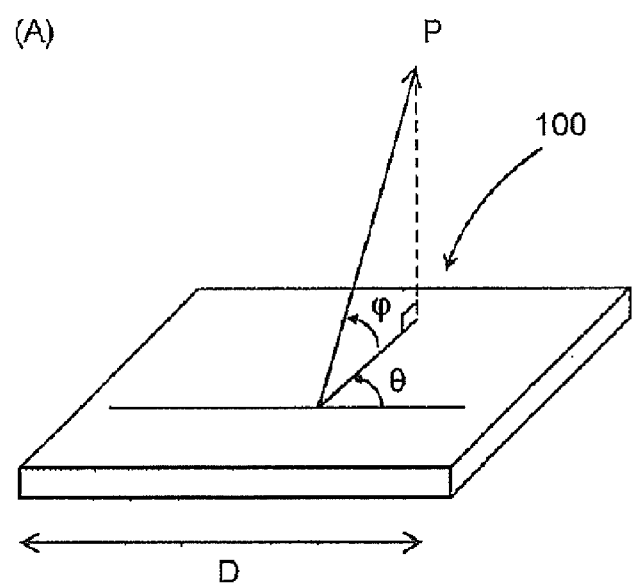
FIG. 2A is a diagram illustrating representation of direction with respect to a sheet of colloidal crystals immobilized in resin.
Figure 2B:
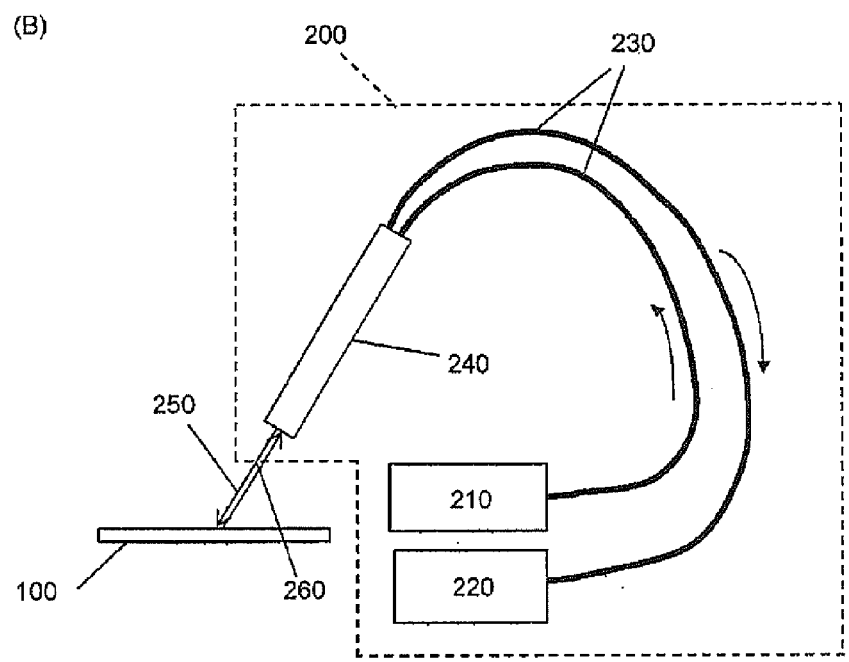
FIG. 2B is a diagram illustrating an optical system to measure back reflection spectrum with respect to the sheet of colloidal crystals immobilized in resin.
Figure 3A:
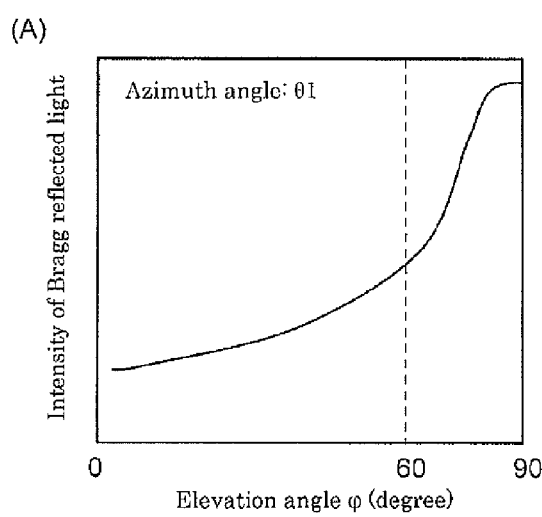
FIG. 3A is a schematic diagram illustrating variation of intensity of Bragg back reflection with respect to an elevation angle obtained from a back reflection spectrum measurement of a sheet of colloidal crystal domains immobilized in resin according to the present invention.
Figure 3B:
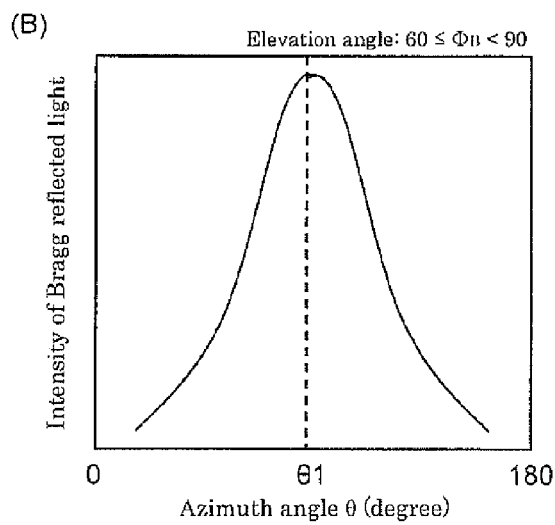
FIG. 3B is a schematic diagram illustrating variation of intensity of Bragg back reflection with respect to an azimuth angle obtained from the back reflection spectrum measurement of the sheet of colloidal crystal domains immobilized in resin according to the present invention.
Figure 3C:
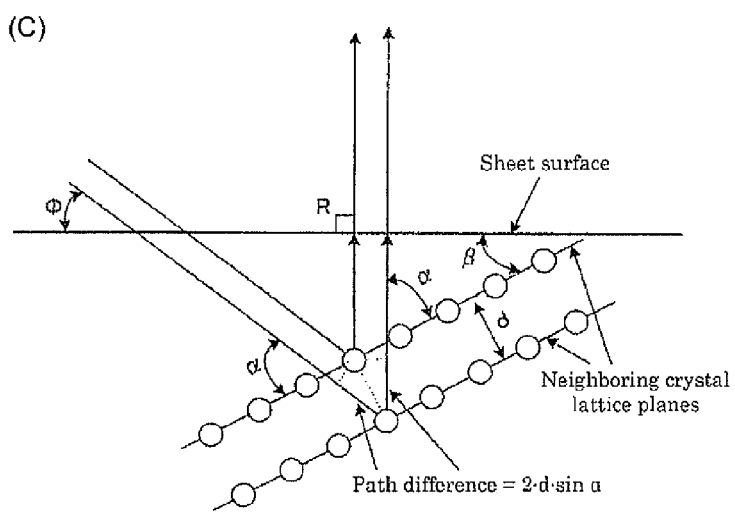
FIG. 3C is a schematic diagram illustrating crystal lattice planes of a crystal domain in the sheet of colloidal crystals immobilized in resin according to the present invention.

FIG. 2A is a diagram illustrating representation of direction with respect to the sheet of colloidal crystals immobilized in resin. FIG. 2B is a diagram illustrating an optical system to measure back reflection spectrum thereof. FIGS. 3A and 3B are schematic diagrams illustrating results of back reflection spectrum measurement of the sheet of colloidal crystal domains immobilized in resin according to the present invention. FIG. 3C is a schematic diagram illustrating crystal lattice planes of a crystal domain.

The sheet of colloidal crystals immobilized in resin 100 according to the present invention satisfies specific conditions as shown in FIGS. 3A and 3B in the back reflection spectrum measurement as shown in FIGS. 2A and 2B, whereby a different effect from the structural color of the known colloidal crystals can be exhibited.

To express the specific direction P with respect to the sheet surface, such as the direction of the incidence axis of irradiation light to the sheet surface and the direction of the reflection axis of reflected light from the sheet surface, the expression utilizing the elevation angle and the azimuth angle, which is customarily used to specify one direction in the three dimensional space, is herein employed. As shown in FIG. 2A, assuming the sheet surface is the horizontal plane, the azimuth angle representing an angle in the horizontal plane is denoted by $\theta$ ($0 \leq \theta$ (degree)<360) and the elevation angle representing an angle in the up-and-down direction based on the horizontal plane as the reference is denoted by $\Phi$ ($0 \leq \Phi$ (degree)$\leq 90$). And, in order to specify the azimuth angle, the reference direction in the horizontal plane is denoted by D.

The azimuth angle $\theta$ of 0 degree and the azimuth angle $\theta$ of 180 degree are in the same direction of D; and the azimuth angle $\theta$ of 90 degree and the azimuth angle $\theta$ of 270 degree are in the same direction orthogonal to the direction D. That is to say, if the azimuth angle $\theta$ is measured at least in the range of not less than 0 degree and not exceeding 90 degree, it can be assumed that all directions in the sheet of colloidal crystals immobilized in resin 100 are measured. And, with respect to the elevation angle $\Phi$, if it is measured in the range of at least 0 degree and not exceeding 90 degree, it can be assumed that all elevation angles with respect to the sheet of colloidal crystals immobilized in resin 100 are measured.

As illustrated in FIG. 2B, a back reflection spectrum measurement is performed using a coaxial fiber spectrometer 200. The coaxial fiber spectrometer 200 comprises a light source 210 and a spectrometer 220. The light source 210 is an arbitrary light source that emits white light. The spectrometer 220 is an arbitrary spectrometer that reads the wavelength and intensity of the spectrum of received light. Illumination light emitted from the light source 210 is applied from a fiber head 240 via an optical fiber 230 onto a sheet of colloidal crystals immobilized in resin 100 serving as a test sample. The fiber head 240 receives only light 260 (namely, back reflected light) that is reflected off the test sample in a direction opposite to the irradiation light 250, and the received light is directed, as detection light, to the spectrometer 220 via the optical fiber 230. In the coaxial fiber spectrometer 200, optic axes, namely an illumination axis and a light receiving axis, are overlapped.

FIG. 3A is a schematic diagram illustrating dependency on the elevation angle of the intensity of Bragg reflection in the case where the azimuth angle $\theta$ is a predetermined angle of $\theta_1$ with respect to the sheet of colloidal crystal domains immobilized in resin 100 according to the present invention. FIG. 3B is a schematic diagram illustrating dependency on the azimuth angle of the intensity of Bragg reflection in the case where the elevation angle $\Phi_B$ (the elevation angle of the incident light of Bragg back reflection) is any angle in the whole range of at least 60 degree and less than 90 degree with respect to the sheet of colloidal crystal domains immobilized in resin 100 according to the present invention.

As shown in FIG. 3A, the intensity of Bragg reflection caused in the plurality of crystal domains 110 of the sheet of colloidal crystals immobilized in resin 100 according to the present invention is not zero (0) in the case where the elevation angle $\Phi_B$ is in the whole range of at least 60 degree and less than 90 degree at the predetermined azimuth angle (Condition (1)). That is, the intensity has a positive value larger than 0. According to Condition (1), since the observation axis of an observer squarely facing the sheet surface of the sheet of colloidal crystals immobilized in resin 100 according to the present invention and the illumination axis of the illumination light do not overlap, the observer squarely facing the sheet surface can easily observe a structural color of the sheet of colloidal crystals immobilized in resin 100. In the case where the sheet of colloidal crystals immobilized in resin 100 according to the present invention is produced by the shearing treatment, a predetermined azimuth angle $\theta_1$ may be set so as to coincide with a direction perpendicular to the shearing direction.

Further, as shown in FIG. 3B, the intensity of Bragg reflection caused in the plurality of crystal domains 110 of the sheet of colloidal crystals immobilized in resin 100 according to the present invention exhibits the maximum value at the predetermined azimuth angle $\theta_1$ with respect to the dependency on the azimuth angle in the entire range in which the elevation angle $\Phi_B$ is at least 60 degree and less than 90 degree (Condition (2)). This Condition (2) allows the sheet of colloidal crystals immobilized in resin 100 according to the present invention to cause the strong color development of the structural color. In FIGS. 3A and 3B, for the sake of simplicity, the shearing direction is denoted by the direction D (i.e., $\theta$ is 0 degree and 180 degree), the case where $\theta_1$ is 90 degree (direction perpendicular to the direction D) is shown as an example.

The following is just inference and may be different from the actual one, but here the structure of the crystal domains, which gives an effect not to overlap the illumination axis and the observation axis of the above-mentioned observer squarely facing the sheet, will be discussed with reference to FIG. 3C. In the sheet of colloidal crystals immobilized in resin in which Bragg back reflection is still exhibited even though the elevation angle is so largely inclined from 90 degree as to become 60 degree, as shown in FIG. 3C, there exist some crystal domains (hereinafter, referred to as simply "inclined crystal domains") having inclined crystal lattice planes at a certain angle (for example, $\beta$) against the sheet surface (sheet face). Therefore, when the illumination light enters at the inclined angle $\Phi$ (elevation angle) into the sheet surface, the incident light enters at the angle of a and is reflected by the same angle in the inclined crystal domains and the direction of this reflection may coincide with the squarely facing direction from general appearance such that an effect of structural coloration caused by Bragg reflection in the squarely facing direction may be exhibited. Here, $\alpha+\beta=90$ degree, and, if the refraction of the incident light on the sheet surface is made negligible, $\alpha=\Phi+\beta$ such that $\Phi=90-2\beta$. That is, the elevation angle $\Phi$ of the incident light corresponding to the direction of the illumination axis become off from the squarely facing direction (90 degree) such that it does not overlap the observation axis. As more accurate consideration, if the refraction of the incident light is considered, $\Phi$ becomes even smaller. That is, the illumination axis become even farther from the observation axis. As configured above, it is inferred that the effect of structural coloration can be exhibited without overlapping the illumination axis and the observation axis.

Further, the significance that the intensity of the Bragg reflection has the maximum value at the specific azimuth angle is considered. It is plausible that, if many crystal domains are inclined at the inclination angle $\beta$ from the sheet surface and oriented to the direction of the specific azimuth angle, they are considered to cause a strong reflection to the squarely facing direction for the illumination from the azimuth angle. In the case where the intensity of the Bragg reflection exhibits the maximum value at the specific azimuth angle, it signifies that a large fraction of crystal domains oriented to the direction at the azimuth angle exist. Therefore, it is inferred that the reflection to the squarely facing direction is more efficiently caused for the illumination from the azimuth angle in such a sheet of colloidal crystals immobilized in resin. Here, the direction of the crystal lattice plane is to be the normal line direction of the crystal lattice plane and the crystal lattice plane oriented to the direction of the specific (predetermined) azimuth angle signifies that the azimuth angel of the normal line direction of the crystal lattice plane is the same as the specific (predetermined) azimuth angle.

From the above-mentioned consideration, in the sheet of colloidal crystal domains immobilized in resin 100 including a plurality of crystal domains, which satisfies Conditions (1) and (2) according to the present invention, some of the plurality of crystal domains have crystal lattice planes inclined (i.e., not parallel) to the sheet surface and further some of the plurality of crystal domains have crystal lattice planes oriented to the direction of the predetermined azimuth angle.

Here, the reason why the value of the elevation angle $\Phi_B$ is to be entire range of at least 60 degree and less than 90 degree is that, from the experimental results, in the case that the intensity of Bragg reflection in the back reflection is not zero (0) in the entire range of the elevation angle is at least 60 degree and less than 90 degree the intensity of the light by Bragg reflection to the squarely facing direction is caused to be so enough as to be visually recognized as the illumination from the direction of the elevation angle 45 degree, which is a typical illumination angle, is made.

In the case where the sheet of colloidal crystals immobilized in resin 100 according to the present invention is produced by the shearing treatment to be mentioned later, the direction of the above-mentioned predetermined azimuth angle may be set to the direction perpendicular to the shearing direction (for example, the direction D in FIG. 2A). As mentioned above, the sheet of colloidal crystals immobilized in resin 100 according to the present invention satisfying surely Conditions (1) and (2) can be obtained.

In the case of colloidal crystals in a polycrystal-like state as shown in Non-patent Reference 1, the direction of the crystal domains is not oriented to the specific direction such that it may be expected that Condition (1) is satisfied, but Condition (2) is not satisfied. On the other hand, in the case of the oriented colloidal crystals as shown in Patent Reference 1 and Non-patent Reference 2, the crystal domains are oriented such that the specific crystal lattice planes are parallel to the sheet surface such that it is expected that neither Condition (1) nor (2) is satisfied. That is, the sheet of colloidal crystals immobilized in resin 100 according to the present invention is a new colloidal crystal having a different structure and different properties from the conventional oriented colloidal crystal and from the colloidal crystal of a polycrystal-like state.

It should be noted that, in FIGS. 1A and 1B, the sheet of colloidal crystals immobilized in resin 100 according to the present invention is illustrated to have gaps between crystal domains 110, but, is not limited to this. The crystal domains 110 may be arranged without gaps therebetween. And it is inferred that the plurality of crystal domains 110 are to be oriented such that the crystal lattice planes thereof are, for example, oriented as shown in FIG. 3C so as to satisfy the above-mentioned Conditions (1) and (2).

In the sheet of colloidal crystals immobilized in resin 100 according to the present invention, the particle concentration of colloidal particles 130 is preferably not less than 2% by volume and not exceeding 35% by volume. When the particle concentration exceeds 35% by volume, the production of the sheet of colloidal crystals immobilized in resin becomes difficult, and there is a possibility of failing to obtain desired characteristics. When the particle volume concentration is less than 2% by volume, sometimes colloidal crystals are not formed in a liquid colloidal dispersion.

The particle concentration is more preferably not less than 5% by volume and not exceeding 25% by volume, and such particle concentration allows desired characteristics to be obtained throughout the entire sheet. The particle concentration is still more preferably not less than 10% by volume and not exceeding 20% by volume, and such particle concentration allows desired characteristics to be surely obtained throughout the entire sheet.

The sheet thickness of the sheet of colloidal crystals immobilized in resin 100 according to the present invention is preferably more than 0.3 mm and not exceeding 10 mm. When the sheet thickness is not exceeding 0.3 mm, colloidal crystals having a specific crystal lattice plane that is oriented parallel to the sheet surface could be formed, and accordingly, sometimes desired characteristics cannot be obtained. When the sheet thickness is more than 10 mm, the production of the sheet becomes difficult. The sheet thickness is more preferably not less than 0.5 mm and not exceeding 5 mm. Such sheet thickness allows desired characteristics to be surely obtained when the sheet of colloidal crystals immobilized in resin 100 is produced by the shearing treatment. The sheet thickness is still more preferably not less than 0.7 mm and not exceeding 3 mm. Such sheet thickness allows desired characteristics to be surely obtained throughout the entire sheet of colloidal crystals immobilized in resin.

Further, the sheet of colloidal crystals immobilized in resin 100 according to the present invention lets the Bragg reflation occur in the angle condition deviated from the squarely facing condition of the sheet surface such that a structural color by Bragg reflection can be observed under the condition that the surface reflected light of the illumination light does not overlap the Bragg reflection light (non-squarely-reflecting condition). Thus, the use of the sheet of colloidal crystals immobilized in resin 100 according to the present invention allows an effect of clearer color development to be produced than in the case of using existing colloidal crystals.

Besides the crystal domains 110 satisfying the above-mentioned Conditions (1) and (2), the sheet of colloidal crystals immobilized in resin 100 according to the present invention may include different crystal domains to the extent that Conditions (1) and (2) are not affected. Alternatively, besides the crystal domains 110, the sheet of colloidal crystals immobilized in resin 100 according to the present invention may include inorganic solids, such as metal, glass, and ceramics, or organic solids, such as plastics.

Figure 4:
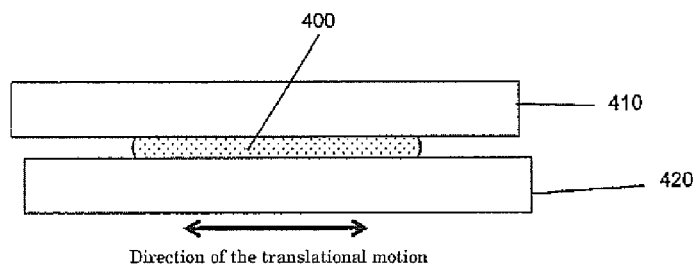
FIG. 4 is a diagram illustrating a state of manufacturing the sheet of colloidal crystals immobilized in resin according to the present invention.

Next, a method of producing the sheet of colloidal crystals immobilized in resin 100 according to the present invention will be described. FIG. 4 is a diagram illustrating a state of manufacturing the sheet of colloidal crystals immobilized in resin according to the present invention. First, a liquid colloidal dispersion is prepared. The liquid colloidal dispersion includes: a liquid dispersion medium comprising a monomer, an oligomer, a macromer, or a combination of these of a compound to be polymerized by ultraviolet irradiation, heating, or the like and thereby form a resin; and colloidal particles dispersed in the liquid dispersion medium. Since the colloidal particles are the same as the colloidal particles 130 (FIG. 1B), a description thereof will be omitted.

An arbitrary compound may be employed if a dispersion medium is in a colloidal crystal state, but, compounds to be polymerized and form an acrylic resin, an epoxy resin, a siloxane resin (silicone), an urethane resin, a polyester resin, an alkyd resin, a fluororesin, and a polyether resin are preferable. Since these resins and compounds to form the resins are the same as the resin 120 (FIG. 1B), a description thereof will be omitted. The dispersion medium may contain an arbitrary polymerization initiator that becomes active by ultraviolet irradiation, heating, or the like.

The particle concentration of the liquid colloidal dispersion is preferably not less than 2% volume and not exceeding 35% by volume. As mentioned above, when the particle concentration exceeds 35% by volume, producing the sheet of colloidal crystals immobilized in resin becomes difficult, and there is a possibility of failing to obtain desired characteristics. When the particle volume concentration is less than 2% by volume, sometimes colloidal crystals are not formed in the liquid colloidal dispersion. The particle concentration is more preferably not less than 5% by volume and not exceeding 25% by volume, and such particle concentration allows desired characteristics to be obtained throughout the entire sheet. The particle concentration is still more preferably not less than 10% by volume and not exceeding 20% by volume, and such particle concentration allows desired characteristics to be surely obtained throughout the entire sheet.

When the thus-prepared liquid colloidal dispersion has a sufficiently low impurity ion concentration, the three-dimensional periodic arrangement of particles is made on an autonomous basis, and the dispersion is in a colloidal crystal state. In the case of a liquid colloidal dispersion having a high impurity ion concentration, bringing the liquid colloidal dispersion into contact with an ion-exchange resin allows the impurity ion concentration to be decreased, and allows the dispersion to fall in a colloidal crystal state.

Next, a thus-prepared colloidal dispersion 400 is sandwiched between two glass plates 410 and 420 that horizontally face each other. One glass plate 410 out of the two is fixed. Then, the other glass plate 420 is imparted vibrational-translational motion linearly in the horizontal direction shown by an arrow in the figure, whereby the sandwiched liquid colloidal dispersion undergoes the shearing treatment. For example, the direction of the vibrational-translational motion (called "shearing direction") is the direction D as illustrated in FIG. 2A. The distance between the surfaces of the glass plates can be the sheet thickness of the sheet of colloidal crystals immobilized in resin 100 to be obtained, and therefore, is preferably more than 0.3 mm and not exceeding 10 mm.

Here, the conditions of the illustrated vibrational-translational motion are as follows. These conditions allow crystal domains of the liquid colloidal dispersion 400 to be so oriented as to satisfy Conditions (1) and (2).

Vibration frequency: 5 to 100 Hz

Vibration amplitude: 1 to 5 times the distance between the surfaces

Processing time: 10 seconds to 10 minutes

More preferably, the conditions of the illustrated vibrational-translational motion are as follows. These conditions allow crystal domains of the liquid colloidal dispersion 400 to be so oriented as to surely satisfy Conditions (1) and (2).

Vibration frequency: 7 to 20 Hz

Vibration amplitude: 1.5 to 2.5 times the distance between the surfaces

Processing time: 30 seconds to 2 minutes

It should be noted that the vibration amplitude may be 1 to 3 times the distance between the surfaces.

After the liquid colloidal dispersion undergoes the shearing treatment, the dispersion medium is polymerized by ultraviolet irradiation, heating, or the like. The sheet of colloidal crystals immobilized in resin 100 according to the present invention is thus obtained.

Embodiment 2

In Embodiment 2, there will be described a method of displaying a structural color by using the sheet of colloidal crystals immobilized in resin described in Embodiment 1.

Figure 5:
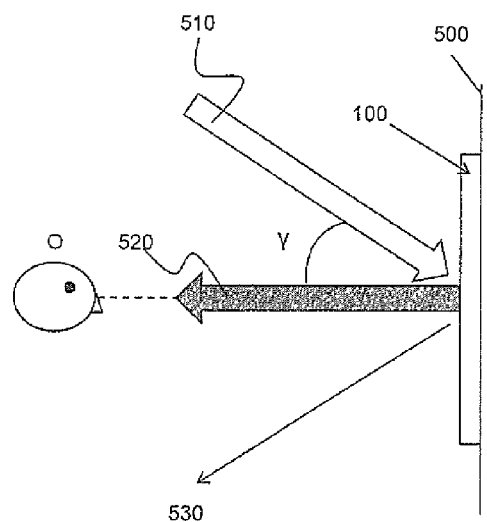
FIG. 5 is a schematic diagram illustrating how a structural color is displayed according to the present invention.

FIG. 5 is a schematic diagram illustrating how a structural color according to the present invention is displayed. In FIG. 5, the sheet of colloidal crystals immobilized in resin 100 described in Embodiment 1 is attached onto a wall 500, and an observer O observes the sheet of colloidal crystals immobilized in resin 100 from a direction squarely facing the sheet surface. The method of displaying a structural color based on colloidal crystals includes the step of irradiating illumination light 510 on the sheet of colloidal crystals immobilized in resin 100. The light source of the illumination light 510 is an arbitrary illuminator, such as a light emitting diode element (LED), a fluorescent lamp, or an incandescent lamp, or natural illumination, such as sunlight. These illuminators may be an existing interior illumination apparatus having been installed.

Specifically, the step of irradiating illumination light 510 is such that illumination light 510 is irradiated on the sheet of colloidal crystals immobilized in resin 100 from a direction different from a direction squarely facing the sheet surface of the sheet of colloidal crystals immobilized in resin 100. Such configuration allows the observer O to observe Bragg reflected light 520 without overlapping of the observation axis of the observer O and the illumination axis of illumination light 510 and without overlapping of surface reflected light 530 of the illumination light 510 and Bragg reflected light 520. More preferably, in the step of irradiating illumination light 510, the direction to emit the illumination light is, for example, a direction perpendicular to the shearing direction in the case where the sheet of colloidal crystals immobilized in resin is produced by the shearing treatment. This allows the observer O to observe strong color development caused by Bragg reflected light 520.

More preferably, in the step of irradiating illumination light 510, the illumination light 510 is irradiated on the sheet of colloidal crystals immobilized in resin 100 at an elevation angle $\Phi$ from the sheet surface in a range of from 30 degree to 60 degree. This range allows the observer O to surely observe strong color development caused by Bragg reflected light 520. The elevation angle $\Phi$ illustrated in FIG. 5 is the same as the elevation angle $\Phi$ illustrated in FIG. 2A. For example, in FIG. 5, when the sheet of colloidal crystals immobilized in resin 100 has a pattern comprising a character or a figure, such pattern can be effectively displayed for the observer O.

Figure 6:
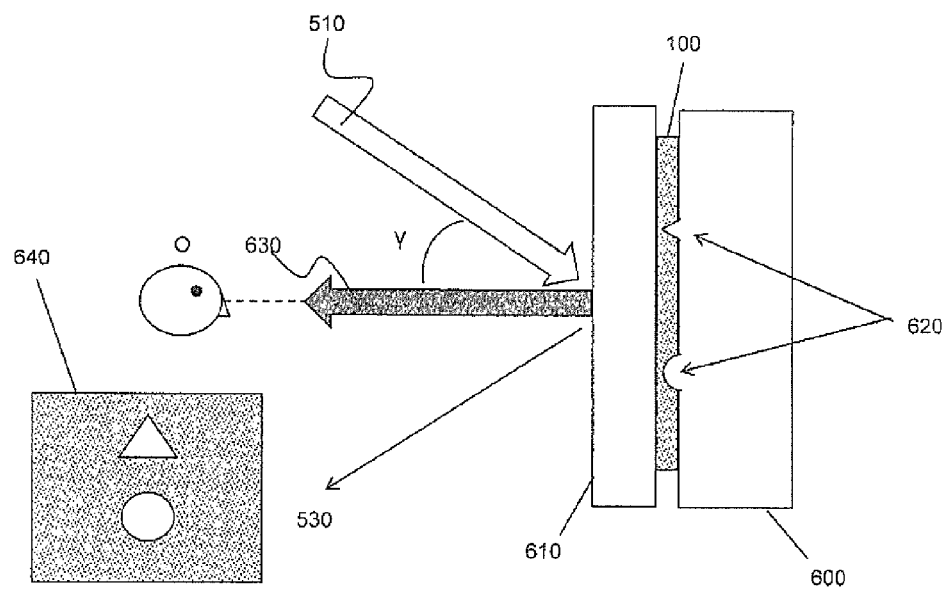
FIG. 6 is a schematic diagram illustrating how a structural color is displayed according to the present invention.

FIG. 6 is another schematic diagram illustrating how a structural color according to the present invention is displayed. In FIG. 6, the sheet of colloidal crystals immobilized in resin 100 described in Embodiment 1 is attached onto a relief plate 600, and an observer O observes the sheet of colloidal crystals immobilized in resin 100 from a direction squarely facing the sheet surface. Here, the resin 120 (FIG. 1B) of the sheet of colloidal crystals immobilized in resin 100 has flexibility and thereby can easily become deformed under a usage environment. Here, the sheet of colloidal crystals immobilized in resin 100 having enough flexibility to easily become deformed denotes that the sheet of colloidal crystals immobilized in resin 100 is in a state in which said sheet can become deformed through a later-mentioned pressing step so as to reflect concave and convex of a pattern 620 of the relief plate 600.

As illustrated in FIG. 6, the sheet of colloidal crystals immobilized in resin 100 is sandwiched at least between a hard transparent plate 610 and the relief plate 600 that has the pattern 620 comprising a character or a figure and expressed by concave and convex. It is beneficial that both of the relief plate 600 and the hard transparent plate 610 have enough hardness not to easily become deformed, and a material to be used for said plates is not particularly limited. The hard transparent plate 610 is transparent enough to allow a structural color of the sheet of colloidal crystals immobilized in resin 100 to be seen. The illustrated hard transparent plate 610 may be a glass plate, an acrylic resin plate, or a polycarbonate resin plate, but, are not limited to these.

An opaque flexible sheet (not illustrated) may be disposed such that the relief plate 600, the opaque flexible sheet, the colloidal crystals immobilized in resin 100, and the hard transparent plate 610 are aligned in this order. The opaque flexible sheet makes it possible to reduce reflection of light from the relief plate 600 other than Bragg reflected light, and therefore, an observer can observe clearer color development of a structural color. Such opaque flexible sheet is a material capable of fitting the pattern 620 of the relief plate 600, and examples of the sheet include a rubber sheet colored in black or the like, colored cloth, and various resin films. Alternatively, also in the case where a surface of the sheet of colloidal crystals immobilized in resin 100, the surface being in contact with the relief plate 600, is painted over with a colored paint, or in the case where a colored rubber paste or the like is applied to said surface, the same effect as in the case of using the opaque flexible sheet can be produced.

A method, illustrated in FIG. 6, for displaying a structural color based on colloidal crystals may include the step of pressing the sheet of colloidal crystals immobilized in resin 100 with the hard transparent plate 610 prior to the step of irradiating illumination light 510 on the sheet of colloidal crystals immobilized in resin 100. The step of irradiating illumination light is the same as the step described with reference to FIG. 5, and therefore a description thereof will be omitted.

By the pressing step, an area of the sheet of colloidal crystals immobilized in resin 100, the area coming into contact with convex of the pattern 620, is pressed and deformed. As a result, the particle spacing between colloidal particles in the pressed and deformed area is different from the particle spacing between colloidal particles in other areas. It should be noted that the pressing step may be performed by mechanically pressing, for example, tightening a screw using a jig, or by manually pressing the hard transparent plate 610 against the sheet of colloidal crystals immobilized in resin 100.

Next, the step of irradiating illumination light 510 on the sheet of colloidal crystals immobilized in resin 100 is performed. This step makes it possible for an observer O to observe Bragg reflected light 630. Specifically, Bragg reflected light 630 is constituted of Bragg reflected light based on the non-deformed area and Bragg reflected light based on the deformed area. That is, an observer O can recognize the pattern 620 comprising convex and concave (unevenness distribution) as the color distribution 640 of a structural color. In the color distribution 640 of a structural color, an area corresponding to the pattern 620 comprising convex and concave is a triangle and a circle. As indicated in the color distribution 640 of a structural color, an observer O recognizes that the structural color of a triangle and a circle (that is, the deformed area) is different from the structural color of an area expressed by hatching (that is, the non-deformed area). Here again, the observer O can observe Bragg reflected light 630 without overlapping of the observation axis of the observer O and the illumination axis of illumination light 510 and without overlapping of surface reflected light 530 of the illumination light 510 and Bragg reflected light 630.

As mentioned above, the use of the sheet of colloidal crystals immobilized in resin according to the present invention allows Bragg reflection to occur even under an angle condition deviated from a regular reflection condition in the sheet surface and accordingly, a structural color caused by Bragg reflection can be observed under a condition where the surface reflected light of illumination light and Bragg reflected light do not overlap (non-regular reflection condition), and thus, an observer can enjoy the effect of clearer color development by irradiation of illumination light. Pressing of the sheet of colloidal crystals immobilized in resin against a relief plate having convex and/or concave allows an observer to visually recognize an unevenness distribution as a color distribution.

Embodiment 3

Figure 7:
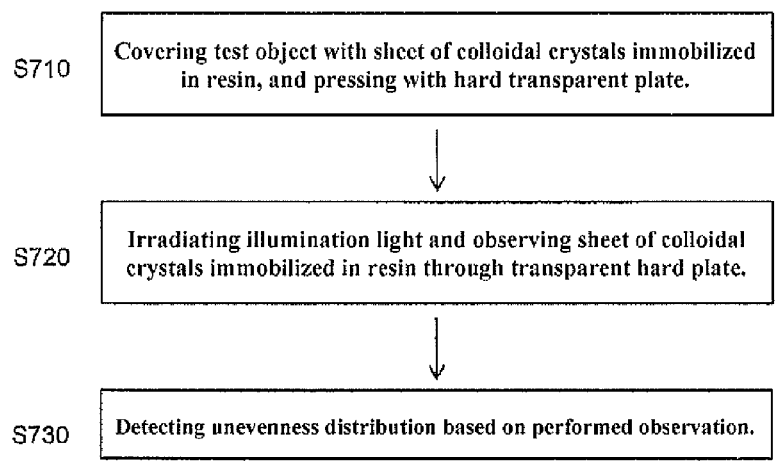
FIG. 7 shows a flowchart illustrating the steps of detecting an unevenness distribution or a hardness distribution of a test object according to the present invention.
Figure 8:
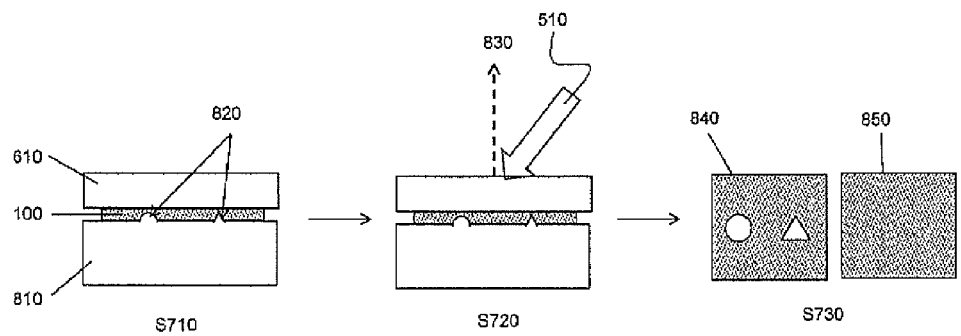
FIG. 8 is a diagram showing procedures indicating the steps of detecting the unevenness distribution of the test object according to the present invention.

In Embodiment 3, a method of detecting the unevenness distribution of a test object using the sheet of colloidal crystals immobilized in resin described in Embodiment 1 is described. FIG. 7 shows a flowchart illustrating the step of detecting the unevenness distribution of a test object according to the present invention. FIG. 8 is a diagram showing procedures indicating the step of detecting the unevenness distribution of a test object according to the present invention.

Step S710: A test object 810 is covered with a sheet of colloidal crystals immobilized in resin 100, and pressed with a hard transparent plate 610. Here, the sheet of colloidal crystals immobilized in resin 100 is the sheet of colloidal crystals immobilized in resin described in Embodiment 1, and a resin in the sheet has flexibility and thereby can easily become deformed under a usage environment. It is beneficial that both of the measurable test object 810 and the hard transparent plate 610 have hardness enough not to easily become deformed, and a material thereof is not particularly limited. The hard transparent plate 610 is the same as the hard transparent plate described in Embodiment 2. In FIG. 8, the test object 810 has a convex portion 820. Here, the sheet of colloidal crystals immobilized in resin 100 having flexibility enough to easily become deformed denotes that the sheet of colloidal crystals immobilized in resin 100 is in a state in which said sheet can become deformed by the pressing step so as to reflect the unevenness distribution (or the hardness distribution) of the test object 810. It should be noted that the pressing step may be performed by mechanically pressing, for example, tightening a screw using a jig, or by manually pressing the hard transparent plate 610 against the sheet of colloidal crystals immobilized in resin 100.

In the step S710, the test object 810 is preferably covered with the sheet of colloidal crystals immobilized in resin 100 through an opaque flexible sheet (not illustrated) interposed therebetween. The opaque flexible sheet makes it possible to reduce reflection of light from the test object 810 other than Bragg reflected light, and accordingly, clearer color development of a structural color can be observed. Such opaque flexible sheet is a material capable of fitting the unevenness distribution of the test object 810, and examples of the sheet include a rubber sheet colored in black or the like, colored cloth, and various resin films. Alternatively, also in the case where, prior to the step S710, a surface of the sheet of colloidal crystals immobilized in resin 100, the surface being in contact with the test object 810, is painted over with a colored paint, or in the case where a colored rubber paste or the like is applied to said surface, the same effect as in the case of using the opaque flexible sheet can be produced. By the step S710, an area of the sheet of colloidal crystals immobilized in resin 100, the area coming into contact with the convex portion 820, is pressed and deformed. As a result, the particle spacing between colloidal particles in the pressed and deformed area is different from the particle spacing between colloidal particles in other areas.

Step S720: Illumination light 510 is irradiated on the sheet of colloidal crystals immobilized in resin 100, and the sheet of colloidal crystals immobilized in resin 100 is observed through the hard transparent plate 610. The illumination light 510 is the illumination light described in Embodiment 2, and the illumination light is irradiated on the sheet of colloidal crystals immobilized in resin 100 in the same manner as in the step, described in Embodiment 2, of irradiating illumination light. The observation may be visual observation, or may be made by photographing using a digital camera or the like or by measuring a reflection spectrum with a spectrometer. By the step S720, Bragg reflected light 830 is observed. Specifically, the Bragg reflected light 830 is constituted of Bragg reflected light based on the non-deformed area and Bragg reflected light based on the deformed area.

Step S730: Based on an observation result obtained in the step S720, the detection of unevenness distribution is performed. Specifically, in the case where an observation result obtained in the step S720 is the color distribution of a structural color that is photographed by a digital camera, the observation result 840 is compared with the color distribution 850 (pre-measurement color distribution) of a structural color of the sheet of colloidal crystals immobilized in resin before the step S710, and if these color distributions are the same, the absence of unevenness distribution in the test object 810 is detected, whereas if these color distributions are different, the presence of unevenness distribution in the test object 810 is detected. In FIG. 8, compared with the pre-measurement color distribution 850, the observation result 840 shows a change of the structural color in an area corresponding to the convex portion 820.

Alternatively, in the step 3730, in the case where an observation result is a reflection spectrum measured throughout the entire area of the sheet of colloidal crystals immobilized in resin 100, said reflection spectrum may be compared with a reflection spectrum measured throughout the entire area of the sheet of colloidal crystals immobilized in resin 100 before the step S710. In this case, if these reflection spectra are the same throughout the entire area of the sheet, the absence of unevenness distribution in the test object 810 is detected, whereas if the reflection spectra are different, the presence of unevenness distribution in the test object 810 is detected. A measurement of a reflection spectrum by using a spectrometer makes it possible to detect an unevenness distribution that is too minute to be visually recognized. Furthermore, the use of such detection result makes mapping of unevenness distribution possible.

With reference to FIGS. 7 and 8, the case where the test object 810 had an unevenness distribution was described in detail, and the same goes for a case where the test object has a hardness distribution. That is, a method of detecting the hardness distribution of a test object according to the present invention includes the steps of: in the same manner as in the step S710, covering the test object with the sheet of colloidal crystals immobilized in resin and pressing the test object with a hard transparent plate; in the same manner as in the step 3720, irradiating illumination light on the sheet of colloidal crystals immobilized in resin and observing said sheet of colloidal crystals immobilized in resin through the hard transparent plate; and, in the same manner as in the step S730, detecting a hardness distribution based on an observation result. Each of the steps is also performed in the same manner as the method of detecting an unevenness distribution, and therefore, detailed descriptions about the steps will be omitted. In the case where the test object has hardness distribution, through the pressing step, an area of the sheet of colloidal crystals immobilized in resin, the area coming into contact with a high hardness portion of the test object, is pressed, thereby becoming deformed, whereas an area of the sheet of colloidal crystals immobilized in resin, the area coming into contact with a low hardness portion of the test object, hardly becomes deformed. As a result, the particle spacing between colloidal particles in the pressed and deformed area is different from the particle spacing between colloidal particles in other areas, and accordingly, in the observation step and the detection step, can be detected as a change in the color distribution of a structural color or a change in reflection spectrum.

Embodiment 4

Figure 9:
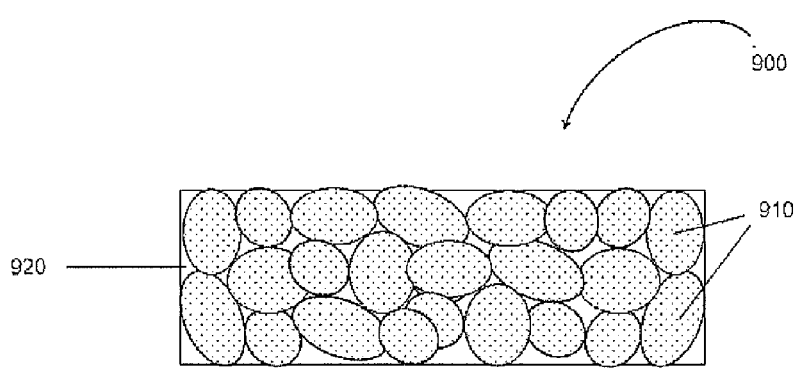
FIG. 9 is a schematic diagram illustrating a structural color sheet according to the present invention.

In Embodiment 4, a structural color sheet produced by using the sheet, described in Embodiment 1, of colloidal crystals immobilized in resin is described. FIG. 9 is a schematic diagram illustrating a structural color sheet according to the present invention. The structural color sheet 900 according to the present invention includes a plurality of sheet pieces of colloidal crystals immobilized in resin 910, and these sheet pieces are immobilized in a resin 920. The plurality of sheet pieces of colloidal crystals immobilized in resin 910 is cut out of the sheet of colloidal crystals immobilized in resin 100 described in Embodiment 1. It should be noted that there is no particular limitation on the shape of cut-out pieces. The plurality of sheet pieces of colloidal crystals immobilized in resin 910 is positioned in the resin 920 in an arbitrary orientation relationship.

The resin 920 denotes a solid material formed of a polymer, such as synthetic resin, plastics, or elastomer, and the same resin as the resin 120 described in Embodiment 1 may be employed. The resin in the plurality of sheet pieces of colloidal crystals immobilized in resin 910 and the resin 920 do not necessarily have to be the same, but, are preferably the same in order to surely exhibit the characteristics of the structural color sheet 900. In the structural color sheet 900 according to the present invention, each of the plurality of sheet pieces of colloidal crystals immobilized in resin 910, as described in detail in Embodiment 1, satisfies (Condition (1)) the intensity of Bragg reflection cause in the plurality of constituting crystal domains is not zero (0) in the entire range where the elevation angle $\Phi_B$ is at least 60 degree and less than 90 degree and (Condition (2)) the intensity of Bragg reflection has the maximum value at the predetermined azimuth angle with respect to the dependency on the azimuth angle. That is, when each of the plurality of sheet pieces of colloidal crystals immobilized in resin 910 is irradiated with illumination light from the direction of a predetermined azimuth angle, the observation axis of an observer squarely facing the sheet surface and the illumination axis of the illumination light do not overlap, and therefore, the observer squarely facing the sheet surface can easily observe a structural color of the sheet pieces of colloidal crystals immobilized in resin 910.

However, in the structural color sheet 900 according to the present invention, such plurality of sheet pieces of colloidal crystals immobilized in resin 910 is positioned in an arbitrary orientation relationship, and therefore, the direction of illumination light is not limited to the direction of a predetermined azimuth angle (for example, a direction perpendicular to the shearing direction), and even in the case of irradiation of illumination light from a direction of an azimuth angle other than the predetermined azimuth angle, there can be brought about a state in which the observation axis of an observer squarely facing the sheet surface and the illumination axis of the illumination light do not overlap, and the surface reflected light of illumination light and Bragg reflected light do not overlap, and accordingly, the observer squarely facing the sheet surface of the structural color sheet 900 can observe a structural color more easily than observe a structural color of a single sheet of colloidal crystals immobilized in resin as a whole.

Although there is no particular limitation on a method of producing the structural color sheet 900 according to the present invention, it is beneficial that, for example, a liquid dispersion is disposed in the form of sheet, and undergoes ultraviolet irradiation, heating, or the like to be polymerized and solidified, the liquid dispersion being obtained by dispersing the plurality of sheet pieces of colloidal crystals immobilized in resin 910 cut out of the sheet of colloidal crystals immobilized in resin 100 in a dispersion medium comprising a monomer, an oligomer, a macromer, or a combination of these of a compound to be polymerized by ultraviolet irradiation, heating, or the like, and thereby to form the resin 920.

It should be noted that the method, described in Embodiment 2, for displaying a structural color may be applied using the structural color sheet 900, or the method, described in Embodiment 3, for detecting the unevenness distribution or the hardness distribution of a test object may be applied using the structural color sheet 900. Also in these cases, in the step of irradiating illumination light, the direction of shinning illumination light is not limited to the direction of a predetermined azimuth angle (for example, a direction perpendicular to the shearing direction), and illumination light may be irradiated from a direction other than the direction of the predetermined azimuth angle, and therefore, there is less limitation on the embodiment of the methods, which is advantageous.

Next, the present invention will be described in detail using specific examples, but, it should be noted that the present invention is not limited to these examples.

EXAMPLES

Example 1

In Example 1, a sheet of colloidal crystals immobilized in resin was produced, the sheet having a particle diameter of 150 nm, a particle concentration 17% by volume, and a sheet thickness of 1 mm, and being flexible and easily deformable at room temperature. A liquid colloidal dispersion was prepared by dispersing silica particles having a particle diameter of 150 nm as colloidal particles in a dispersion medium obtained by adding an ultraviolet-activated polymerization initiator to a liquid monomer of a compound, 4-hydroxybutyl acrylate (4-HBA). The particle concentration of the liquid colloidal dispersion was 17% by volume. It was confirmed that the liquid colloidal dispersion visually exhibited a play-of-color effect and was in a colloidal crystal state. This liquid colloidal dispersion was sandwiched between two glass plates that horizontally face each other as illustrated in FIG. 4, and the upper one of the glass plates was fixed, while the lower one of the glass plates was imparted vibrational-translational motion linearly in the horizontal direction, whereby the sandwiched liquid colloidal dispersion undergoes the shearing treatment. The distance between the surfaces, facing each other, of the two glass plates was 1 mm. The direction of the vibrational-translational motion (i.e., shearing direction) was the direction D (FIGS. 2A and 4).

The conditions of the vibrational-translational motion were as follows.

Vibration frequency: 10 Hz

Vibration amplitude: twice the distance between the surfaces

Processing time: 1 minute

The shearing treatment brought an orientation state in which the entire surface of the liquid colloidal dispersion assumed a uniform structural color. Subsequently, ultraviolet irradiation was performed to polymerize and solidify the dispersion medium, whereby a 1-mm-thick sheet of colloidal crystals immobilized in resin was produced. By polymerization, 4-HBA was made into an acrylic resin being easily elastic deformable at room temperature (that is, highly flexible), and accordingly, the obtained sheet of colloidal crystals immobilized in resin (hereinafter, simply referred to as a sample of Example 1) was also an easily elastic deformable material.

Figure 10A:
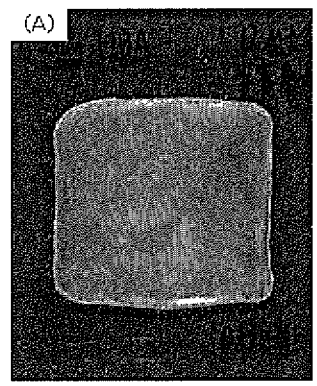
FIG. 10A is a diagram illustrating an observation result of a structural color of a sample of Example 1.
Figure 10B:
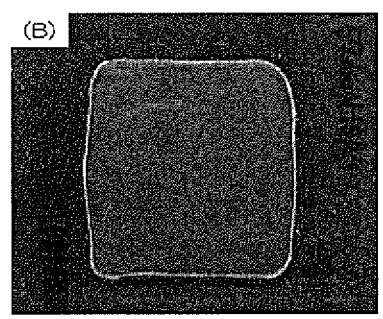
FIG. 10B is a diagram illustrating the observation result of the structural color of the sample of Example 1.

Next, visual observation and photograph evaluation of the sample of Example 1 were carried out. In reference to FIG. 2A, the direction D was the same as the shearing direction with the sample of Example 1. From the elevation angle Φ of 45 degree and the azimuth angle θ of 90 degree, the sample of Example 1 was irradiated with fluorescent light, and observed from a direction squarely facing the sheet surface of the sample of Example 1 (that is, the direction of the elevation angle Φ of 90). FIG. 10A shows the result. Here, θ=90 degree denotes a direction perpendicular to the shearing direction and hence is substantially equivalent to 270 degree. This is because the shearing treatment is performed by the reciprocating motion (hereinafter the same). From a direction having an azimuth angle θ of 0 degree and an elevation angle Φ of 45 degree, the sample of Example 1 was irradiated with fluorescent light, and observed from a direction squarely facing the sheet surface of the sample of Example 1. FIG. 10B shows the result. Here, the shearing treatment is performed by the reciprocating motion, and therefore, θ=0 degree denotes the shearing direction D, and hence is substantially equivalent to 180 degree (hereinafter the same).

Next, using an optical system (a coaxial fiber spectrometer) illustrated in FIG. 2B, a back reflection spectrum (the dependence of reflection intensity on wavelength) of the sample of Example 1 was measured. The wavelength measurement range was 400 nm to 700 nm. Measurement apparatuses used here were: multichannel spectrometer S-2600 manufactured by SOMA OPTICS, LTD., as a spectrometer; a fiber connection type halogen lamp manufactured by the same company, as a light source; and a two-way diffused-reflection probe manufactured by the same company, as an optical fiber and a fiber head.

Figure 16A:
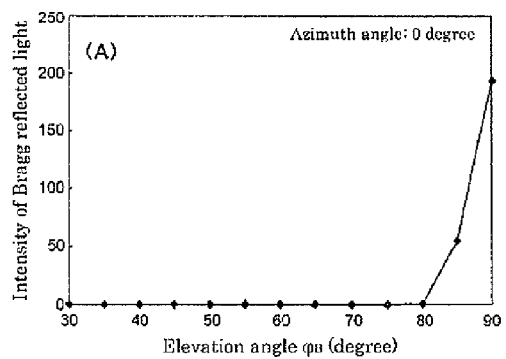
FIG. 16A is a diagram illustrating dependency on the elevation angle of the intensity of Bragg reflection of the sample of Example 1.
Figure 16B:
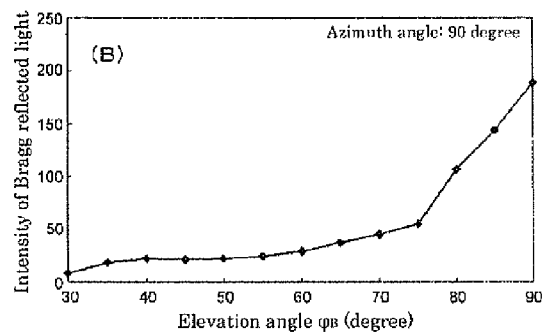
FIG. 16B is a diagram illustrating dependency on the elevation angle of the intensity of Bragg reflection of the sample of Example 1.
Figure 17A:
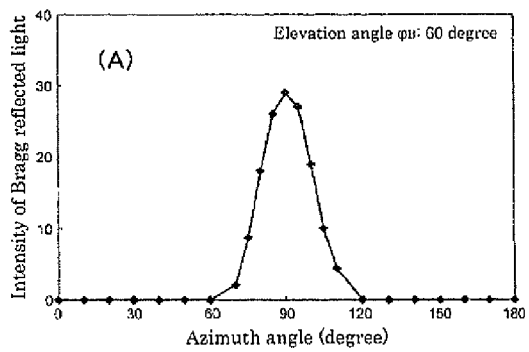
FIG. 17A is a diagram illustrating dependency on the azimuth angle of the intensity of Bragg reflection of the sample of Example 1.
Figure 17B:
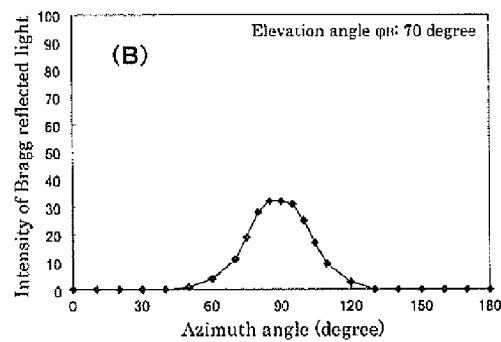
FIG. 17B is a diagram illustrating dependency on the azimuth angle of the intensity of Bragg reflection of the sample of Example 1.
Figure 17C:
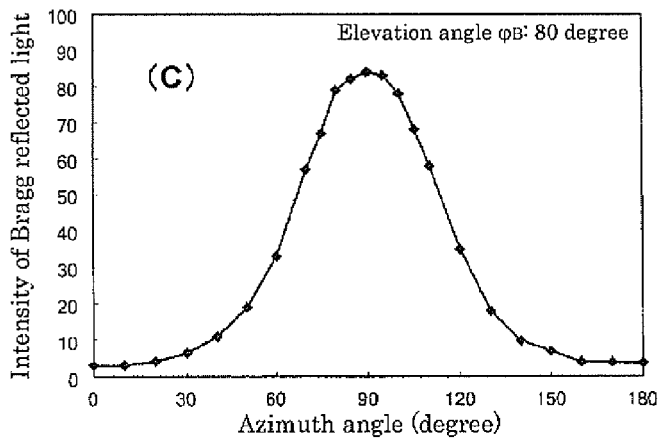
FIG. 17C is a diagram illustrating dependency on the azimuth angle of the intensity of Bragg reflection of the sample of Example 1.

First, for the sample of Example 1, the azimuth angle of a measurement axis was fixed in the same direction as the shearing direction D (θ=0 degree or 180 degree in FIG. 2A), and the dependence of Bragg reflection intensity on the elevation angle on the sheet surface was measured. Next, for the sample of Example 1, the azimuth angle of the measurement axis was fixed in the direction (θ=90 degree or 270 degree in FIG. 2A) perpendicular to the shearing direction D, and the dependence of Bragg reflection intensity on the elevation angle on the sheet surface was measured. FIGS. 16A and 16B show the results. Furthermore, for the sample of Example 1, the elevation angle $\Phi_B$ of the measurement axis was fixed in 1 degree increments in a range of from 60 degree to 90 degree, and the azimuth angle dependence of Bragg reflection intensity was measured. FIGS. 17A to 17C show some results. Here, in the case where a plurality of Bragg back reflection peaks are present in the back reflection spectrum, the maximum peak intensity is adopted. On the other hand, in the case where no peak is present, the peak intensity is regarded as zero. It should be noted that a peak intensity value is represented by a value relative to a back reflection intensity taken as 100, the back reflection intensity being measured using white copy paper as a reference sample and obtained when the elevation angle is 90 degree.

Example 2

In Example 2, a sheet of colloidal crystals immobilized in resin was produced, the sheet having a particle diameter of 150 nm, a particle concentration 11% by volume, and a sheet thickness of 1 mm, and being flexible and easily deformable at room temperature. The production conditions of the sheet of colloidal crystals immobilized in resin in Example 2 are the same as those in Example 1, except that the particle concentration is different from that in Example 1, and therefore, a further description of the conditions will be omitted. As in the case of Example 1, the sample of Example 2 was visually observed and photographically evaluated.

Example 3

In Example 3, a sheet of colloidal crystals immobilized in resin was produced, the sheet having a particle diameter of 180 nm, a particle concentration 17% by volume, and a sheet thickness of 1 mm, and being flexible and easily deformable at room temperature. The production conditions of the sheet of colloidal crystals immobilized in resin in Example 3 are the same as those in Example 1, except that the particle diameter is different from that in Example 1, and therefore, a further description of the conditions will be omitted. As in the case of Example 1, the sample of Example 3 was visually observed and photographically evaluated.

Example 4

Figure 11A:
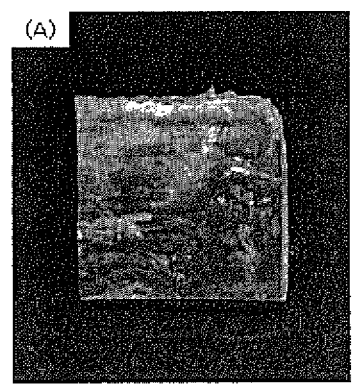
FIG. 11A is a diagram illustrating an observation result of a structural color of a sample of Example 4.
Figure 11B:
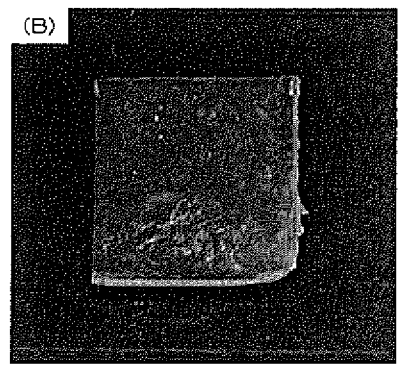
FIG. 11B is a diagram illustrating the observation result of a structural color of the sample of Example 4.
Figure 18A:
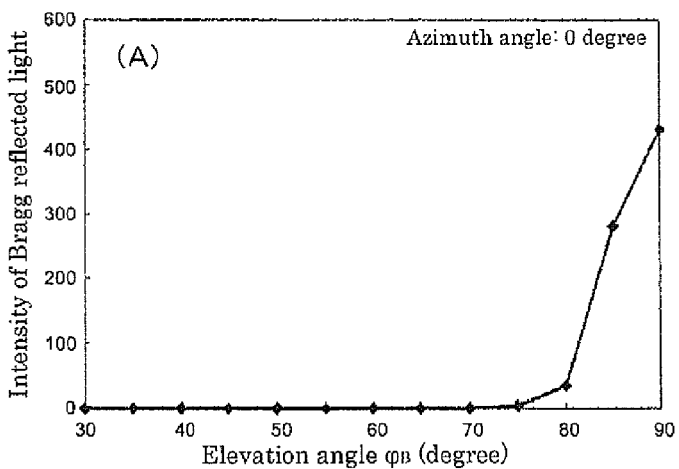
FIG. 18A is a diagram illustrating dependency on the elevation angle of the intensity of Bragg reflection of the sample of Example 4.
Figure 18B:
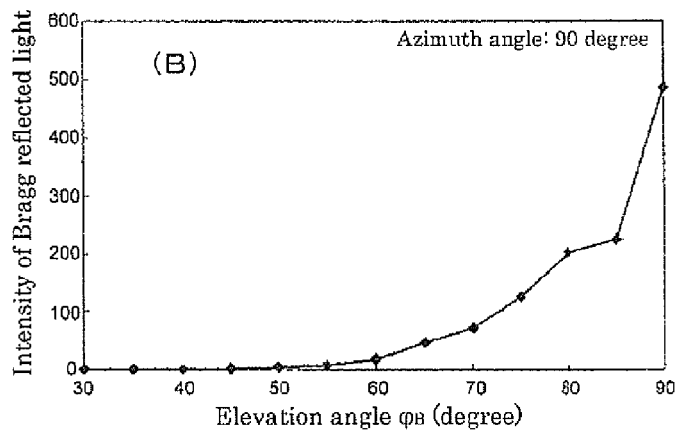
FIG. 18B is a diagram illustrating dependency on the elevation angle of the intensity of Bragg reflection of the sample of Example 4.
Figure 19:
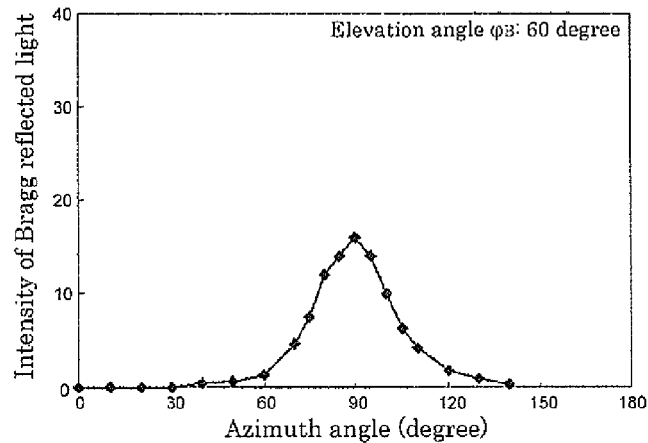
FIG. 19 is a diagram illustrating dependency on the azimuth angle of the intensity of Bragg reflection of the sample of Example 4.

In Example 4, a sheet of colloidal crystals immobilized in resin was produced, the sheet having a particle diameter of 180 nm, a particle concentration 32% by volume, and a sheet thickness of 1 mm, and being flexible and easily deformable at room temperature. The production conditions of the sheet of colloidal crystals immobilized in resin in Example 4 are the same as those in Example 1, except that the particle diameter and the particle concentration are different from those in Example 1, and therefore, a further description of the conditions will be omitted. As in the case of Example 1, the sample of Example 4 was visually observed and photographically evaluated. As in the case of Example 1, a back reflection spectrum of the sample of Example 4 was measured. These results are shown in FIG. 11A (θ=90 degree, Φ=45 degree), FIG. 11B (θ=0 degree, Φ=45 degree), FIG. 18A (θ=0 degree), FIG. 18B (θ=90 degree), and FIG. 19 ($\Phi_B$=60 degree).

Example 5

Figure 12A:
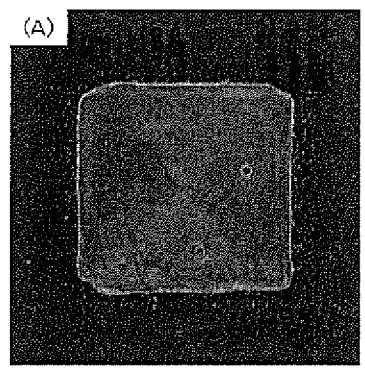
FIG. 12A is a diagram illustrating an observation result of a structural color of a sample of Example 5.
Figure 12B:
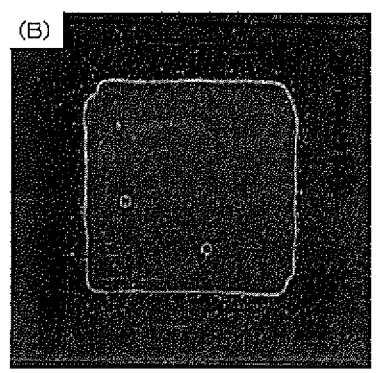
FIG. 12B is a diagram illustrating the observation result of a structural color of the sample of Example 5.
Figure 20A:
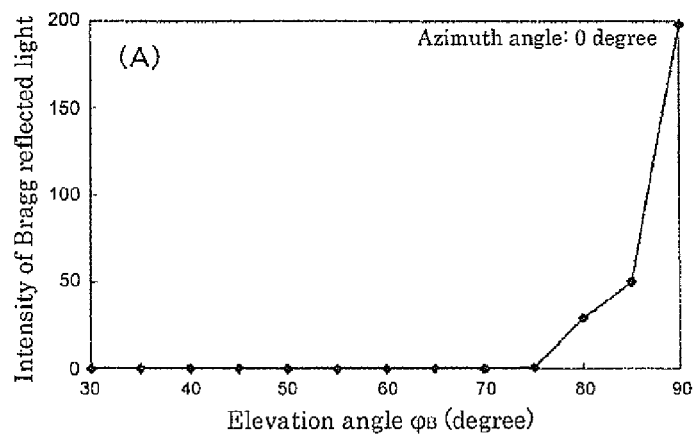
FIG. 20A is a diagram illustrating dependency on the elevation angle of the intensity of Bragg reflection of the sample of Example 5.
Figure 20B:
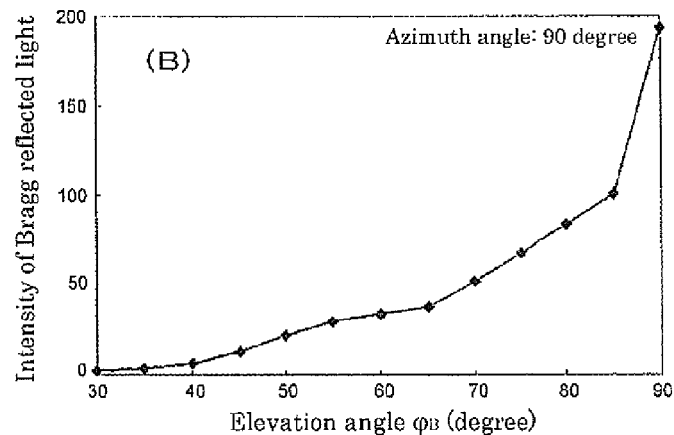
FIG. 20B is a diagram illustrating dependency on the elevation angle of the intensity of Bragg reflection of the sample of Example 5.
Figure 21:
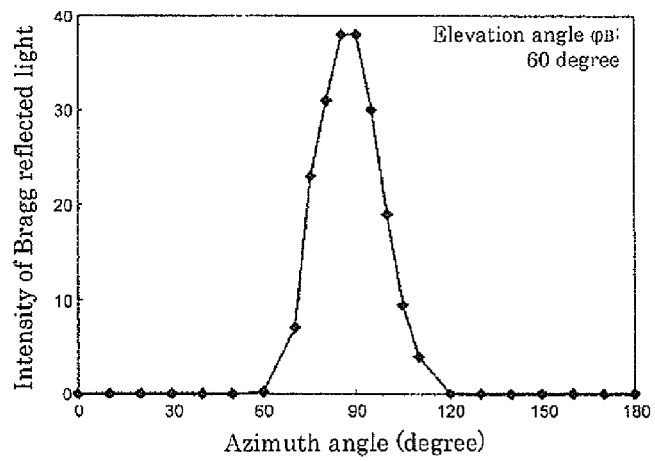
FIG. 21 is a diagram illustrating dependency on the azimuth angle of the intensity of Bragg reflection of the sample of Example 5.

In Example 5, a sheet of colloidal crystals immobilized in resin was produced, the sheet having a particle diameter of 150 nm, a particle concentration 17% by volume, and a sheet thickness of 0.5 mm, and being flexible and easily deformable at room temperature. The production conditions of the sheet of colloidal crystals immobilized in resin in Example 5 are the same as those in Example 1, except that the sheet thickness is different from that in Example 1, and therefore, a further description of the conditions will be omitted. As in the case of Example 1, the sample of Example 5 was visually observed and photographically evaluated. As in the case of Example 1, a back reflection spectrum of the sample of Example 5 was measured. These results are shown in FIG. 12A ($\theta$=90 degree, $\Phi$=45 degree), FIG. 12B ($\theta$=0 degree, $\Phi$=45 degree), FIG. 20A ($\theta$=0 degree), FIG. 20B ($\theta$=90 degree), and FIG. 21 ($\Phi_B$=60 degree).

Example 6

Figure 13A:
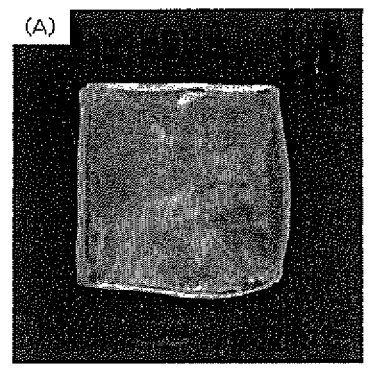
FIG. 13A is a diagram illustrating an observation result of a structural color of a sample of Example 6.
Figure 13B:
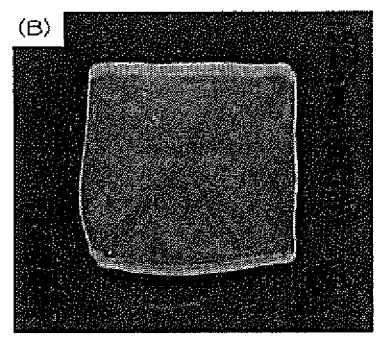
FIG. 13B is a diagram illustrating the observation result of a structural color of the sample of Example 6.
Figure 22A:
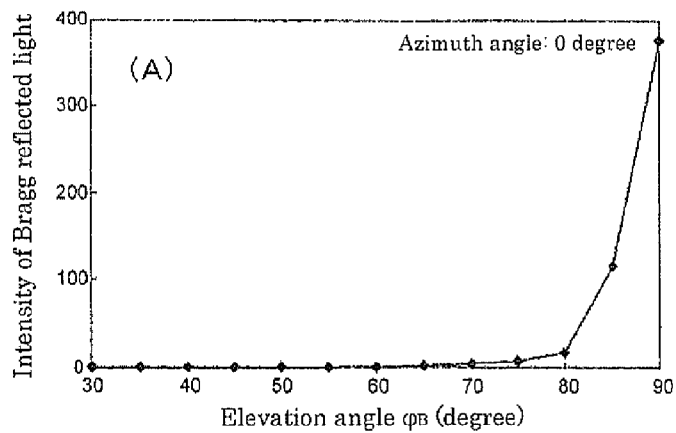
FIG. 22A is a diagram illustrating dependency on the elevation angle of the intensity of Bragg reflection of the sample of Example 6.
Figure 22B:
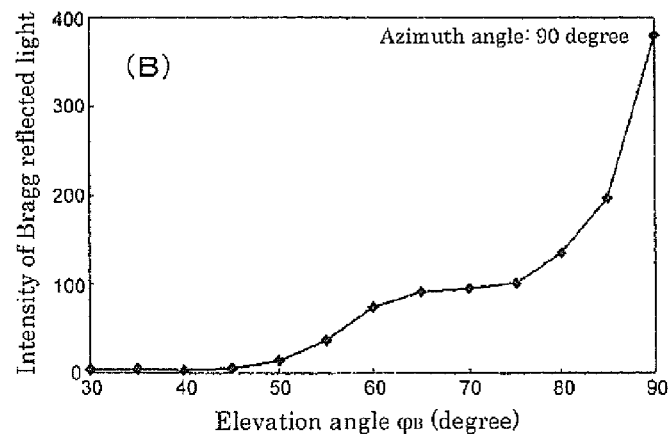
FIG. 22B is a diagram illustrating dependency on the elevation angle of the intensity of Bragg reflection of the sample of Example 6.
Figure 23:
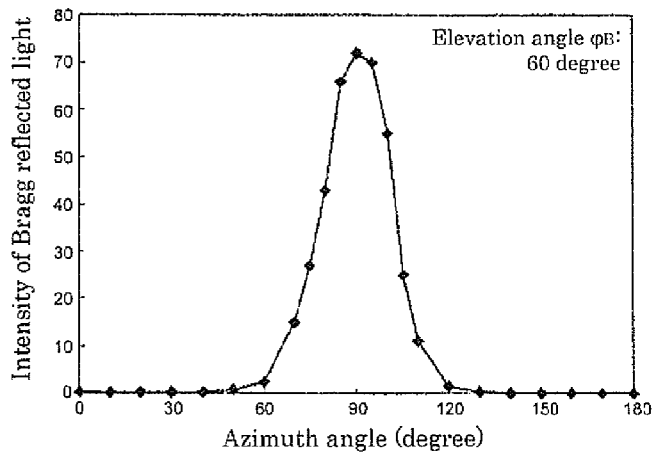
FIG. 23 is a diagram illustrating dependency on the azimuth angle of the intensity of Bragg reflection of the sample of Example 6.

In Example 6, a sheet of colloidal crystals immobilized in resin was produced, the sheet having a particle diameter of 150 nm, a particle concentration 17% by volume, and a sheet thickness of 1 mm, and having a high hardness, thereby being undeformable at room temperature. The production conditions of the sheet of colloidal crystals immobilized in resin in Example 6 are the same as those in Example 1, except that a liquid monomer of a compound, 2-hydroxyethyl methacrylate (2-HEMA), to form an acrylic resin having a high hardness at room temperature was used as a dispersion medium, and therefore, a further description of the conditions will be omitted. As in the case of Example 1, the sample of Example 6 was visually observed and photographically evaluated. As in the case of Example 1, a back reflection spectrum of the sample of Example 6 was measured. These results are shown in FIG. 13A ($\theta$=90 degree, $\Phi$=45 degree), FIG. 13B ($\theta$=0 degree, $\Phi$=45 degree), FIG. 22A ($\theta$=0 degree), FIG. 22B ($\theta$=90 degree), and FIG. 23 ($\Phi_B$=60 degree).

Example 7

In Example 7, a sheet of colloidal crystals immobilized in resin was produced, the sheet having a particle diameter of 150 nm, a particle concentration 17% by volume, and a sheet thickness of 2 mm, and having a high hardness, thereby being undeformable at room temperature. The production conditions of the sheet of colloidal crystals immobilized in resin in Example 7 are the same as those in Example 6, and therefore, a further description of the conditions will be omitted. As in the case of Example 1, the sample of Example 7 was visually observed.

Comparative Example 8

Figure 14A:
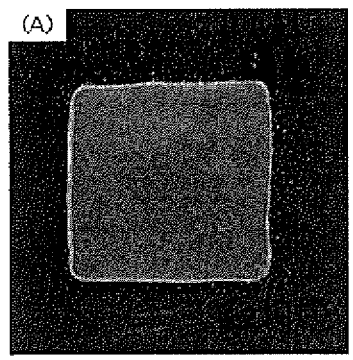
FIG. 14A is a diagram illustrating an observation result of a structural color of a sample of Comparative Example 8.

In Comparative Example 8, a sheet of colloidal crystals immobilized in resin was produced, the sheet having a particle diameter of 150 nm, a particle concentration 17% by volume, and a sheet thickness of 1 mm, and being flexible and easily deformable at room temperature, the colloidal crystals being in a polycrystal-like state (for example, corresponding to colloidal crystals described in Non-patent Reference 1). As in the case of Example 1, a liquid colloidal dispersion was prepared, and sandwiched between two glass plates horizontally facing each other as illustrated in FIG. 4. Without the shearing treatment, the liquid colloidal dispersion underwent ultraviolet irradiation as it was to polymerize and solidify a dispersion medium. Thus, the sheet of colloidal crystals immobilized in resin, the colloidal crystals being in a polycrystal-like state, was obtained. As in the case of Example 1, the sample of Comparative Example 8 was visually observed and photographically evaluated. As in the case of Example 1, a back reflection spectrum of the sample of Comparative Example 8 was measured. It should be noted that, since the shearing treatment was not performed, the direction of translation motion of the glass plates in the case of executing the shearing treatment was taken as the direction D. These results are shown in FIG. 14A ($\theta$=90 degree, $\Phi$=45 degree), FIG. 14B ($\theta$=0 degree, $\Phi$=45 degree), FIG. 24A ($\theta$=0 degree), FIG. 24B ($\theta$=90 degree), and FIG. 25 ($\Phi_B$=60 degree).

Comparative Example 9

Figure 15A:
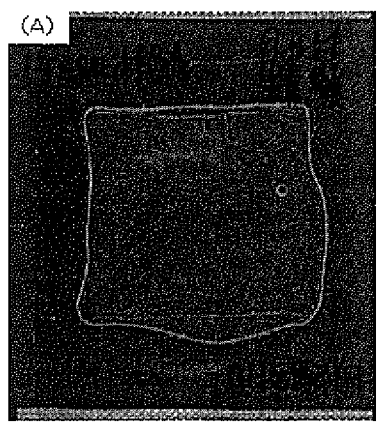
FIG. 15A is a diagram illustrating an observation result of a structural color of a sample of Comparative Example 9.
Figure 15B:
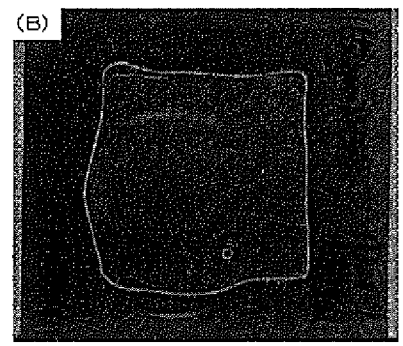
FIG. 15B is a diagram illustrating the observation result of a structural color of the sample of Comparative Example 9.
Figure 26A:
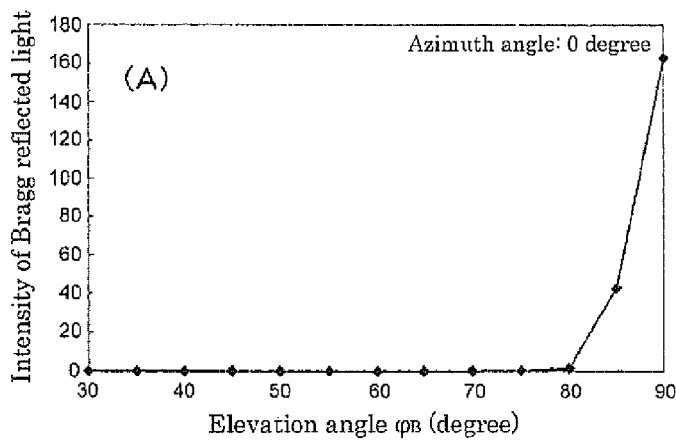
FIG. 26A is a diagram illustrating dependency on the elevation angle of the intensity of Bragg reflection of the sample of Comparative Example 9.
Figure 26B:
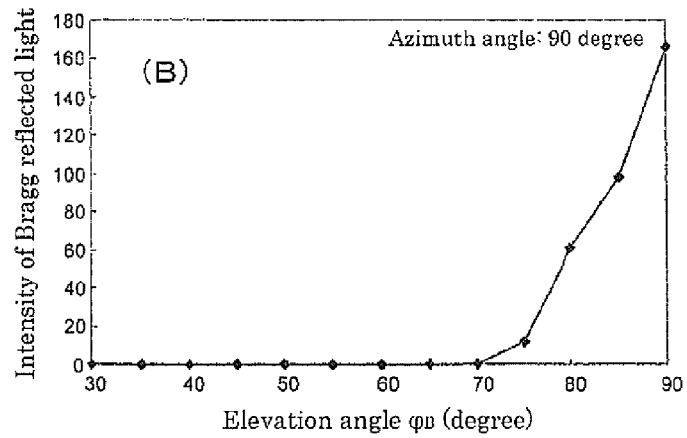
FIG. 26B is a diagram illustrating dependency on the elevation angle of the intensity of Bragg reflection of the sample of Comparative Example 9.
Figure 27:
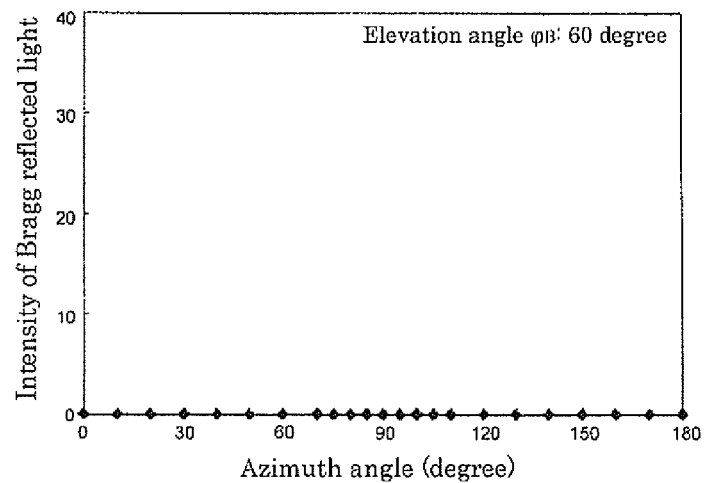
FIG. 27 is a diagram illustrating dependency on the azimuth angle of the intensity of Bragg reflection of the sample of Comparative Example 9.

In Comparative Example 9, a sheet of surface-oriented colloidal crystals (for example, corresponding to colloidal crystals described in Non-patent Reference 2) immobilized in resin was produced, the sheet having a particle diameter of 150 nm, a particle concentration 17% by volume, and a sheet thickness of 0.3 mm, and being flexible and easily deformable at room temperature. The production conditions of the sheet of colloidal crystals immobilized in resin in Comparative Example 9 are the same as those in Example 1, except that the sheet thickness is different from that in Example 1, and therefore, a further description of the conditions will be omitted. As in the case of Example 1, the sample of Comparative Example 9 was visually observed and photographically evaluated. As in the case of Example 1, a back reflection spectrum of the sample of Comparative Example 9 was measured. These results are shown in FIG. 15A ($\theta$=90 degree, $\Phi$=45 degree), FIG. 15B ($\theta$=0 degree, $\Phi$=45 degree), FIG. 26A ($\theta$=0 degree), FIG. 26B ($\theta$=90 degree), and FIG. 27 ($\Phi_B$=60 degree).

Example 10

In Example 10, a sheet of colloidal crystals immobilized in resin was produced, the sheet having a particle diameter of 150 nm, a particle concentration 17% by volume, and a sheet thickness of 1 mm, and having a high hardness, thereby being undeformable at room temperature. The production conditions of the sheet of colloidal crystals immobilized in resin in Example 10 are the same as those in Example 1, except that a compound to form an epoxy resin as a resin having a high hardness at room temperature was used in place of 4-HBA (a compound to form an acrylic resin) in Example 1, and the compound was polymerized by heating. The details are as follows. The compound to form an epoxy resin included bisphenol-A diglycidyl ether as a base and 4-methylhexahydrophthalic anhydride as a curing agent. A liquid obtained by blending the base with the curing agent at a weight ratio of 1:1 was used as a dispersion medium, and silica particles were dispersed in the dispersion medium to prepare a liquid dispersion. This liquid dispersion was made to undergo the shearing treatment under the same conditions as those in Example 1, and subsequently heated to polymerize and solidify the dispersion medium, whereby a 1-mm-thick sheet of colloidal crystals immobilized in resin was obtained. As in the case of Example 1, the sample of Example 10 was visually observed.

For the sake of simplicity, the above-mentioned experimental conditions of Examples and Comparative Examples 1 to 10 are summarized in Table 1.

TABLE 1

List of the experimental conditions of Examples and Comparative Examples 1-10

| Example | | Particle diameter (nm) | Resin | | | Particle concentration (vol %) | Sheet thickness (nm) |
| --- | --- | --- | --- | --- | --- | --- | --- |
| | | | Characteristics @ Room Temperature | Kind | Compound | | |
| Example | 1 | 150 | Deformable | Acrylic resin | 4-HBA | 17 | 1 |
| Example | 2 | 150 | Deformable | Acrylic resin | 4-HBA | 11 | 1 |
| Example | 3 | 180 | Deformable | Acrylic resin | 4-HBA | 17 | 1 |
| Example | 4 | 180 | Deformable | Acrylic resin | 4-HBA | 32 | 1 |
| Example | 5 | 150 | Deformable | Acrylic resin | 4-HBA | 17 | 0.5 |
| Example | 6 | 150 | Undeformable | Acrylic resin | 2-HEMA | 17 | 1 |
| Example | 7 | 150 | Undeformable | Acrylic resin | 2-HEMA | 17 | 2 |
| Comparative Example | 8 | 150 | Deformable | Acrylic resin | 4-HBA | 17 | 1 |
| Comparative Example | 9 | 150 | Deformable | Acrylic resin | 4-HBA | 17 | 0.3 |
| Example | 10 | 150 | Undeformable | Epoxy resin | Bisphenol-A diglycidyl ether, 4-methylhexahydro-phthalic anhydride | 17 | 1 |

FIGS. 10A, 11A, 12A, 13A, 14A, and 15A show results of observation from the squarely facing direction to the sheet surface of the samples as they were irradiated with fluorescent light from the direction each having an azimuth angle θ of 90 degree and an elevation angle Φ of 45 degree. FIGS. 10B, 11B, 12B, 13B, 14B, and 15B show results of observation from the squarely facing direction to the sheet surface of the samples as they were irradiated with fluorescent light from the direction each having an azimuth angle θ of 0 degree and an elevation angle Φ of 45 degree.

In all of FIGS. 10A, 11A, 12A, and 13A, color development of a structural color (blue) by Bragg reflection was clearly observed. In none of FIGS. 10B, 11B, 12B, and 13B, color development of a structural color by Bragg reflection was not substantially observed. Although not illustrated, it was confirmed that, also in the sample of Example 7, the same color development of a structural color as that in Example 6 was obtained. It should be noted that, compared with the sample of Example 4, the samples of Examples 1 to 3, 5, and 6 were more excellent in sheet uniformity. Hence, it is suggested that a particle concentration of not exceeding 35% by volume is preferable.

Likewise, the samples of Examples 2 and 3 were also irradiated with fluorescent light from a direction having an azimuth angle θ of 90 degree and an elevation angle Φ of 45 degree, and observed from a direction squarely facing the sheet surface of the sample, and as a result, although not illustrated, color development of a structural color (red) by Bragg reflection was clearly observed. Likewise, the sample of Example 10 was also irradiated with fluorescent light from a direction having an azimuth angle θ of 90 degree and an elevation angle Φ of 45 degree, and observed from a direction squarely facing the sheet surface of the sample, and as a result, color development of a structural color (blue) by Bragg reflection was clearly observed.

Examples 1 to 7, and 10 showed that changes in the particle diameter and the particle concentration of colloidal particles make it possible to achieve color development of different structural colors. It should be noted that a person skilled in the art is capable of suitably selecting the particle diameter and the particle concentration, thereby controlling the wavelength of Bragg reflection and setting a desired structural color.

Figure 14B:
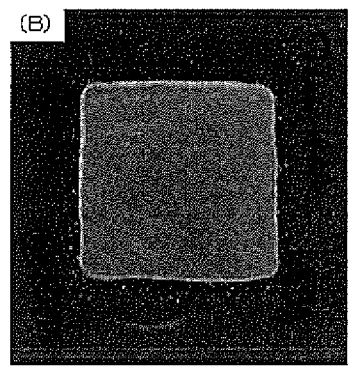
FIG. 14B is a diagram illustrating the observation result of a structural color of the sample of Comparative Example 8.

According to FIGS. 14A and 14B, color development of an extremely-weak structural color (blue) by Bragg reflection was clearly observed. On the other hand, according to FIGS. 15A and 15B, color development of a structural color by Bragg reflection was not observed.

Hence, it was found that, even when the samples of Examples 1 to 7, and 10 are irradiated obliquely with respect to a direction perpendicular to the shearing direction D, as the direction of a predetermined azimuth angle $θ_1$, an observer squarely facing the sheet surfaces of the samples can observe a structural color. Furthermore, when the observation results of the structural colors of the samples of Examples 1 to 7 were compared with that of the sample of Comparative Example 8, it was shown that the structural color of the samples of Examples 1 to 7 can be more clearly observed than that of the sample of Comparative Example 8. Furthermore, when the observation results of the structural color of the samples of Examples 1 to 7 were compared with those of the samples of Comparative Examples 8 and 9, it was shown that, unlike the crystal domains of the sample of Comparative Example 8, the plurality of crystal domains constituting the samples of Examples 1 to 7 did not gather in a disordered orientation relationship, and, unlike the crystal domains of the sample of Comparative Example 9, the crystal domains of the samples of Examples 1 to 7 did not gather orderly in a specific orientation, and it is suggested that, although the details of the aspect of such gathering have not been solved yet at the moment, the gathering is a fairly novel arrangement.

Furthermore, the observation results of Examples 1 to 7, and 10 showed that irradiating illumination light on a sheet of colloidal crystals immobilized in resin according to the present invention makes it possible to display a structural color. Specifically, irradiating illumination light from a direction different from a direction squarely facing the sheet surface of the sheet of colloidal crystals immobilized in resin according to the present invention, more preferably from a direction perpendicular to the shearing direction makes it possible to display a structural color clearly.

Each of FIGS. 16A, 18A, 20A, 22A, 24A, and 26A shows the elevation angle dependence of Bragg reflection intensity of a corresponding one of the samples in the case where an azimuth angle θ is fixed at 0 degree. Each of FIGS. 16B, 18B, 20B, 22B, 24B, and 26B shows the elevation angle dependence of Bragg reflection intensity of a corresponding one of the samples in the case where an azimuth angle θ is fixed at 90 degree.

From FIGS. 16A and 16B, it was found that, in the sample of Example 1, Bragg reflection does not occur in the shearing direction D (θ=0 degree or 180 degree) when an elevation angle $\Phi_B$ was not in the neighborhood of 90 degree, whereas Bragg reflection occurs in a direction (θ=90 degree or 270 degree) perpendicular to the shearing direction D throughout the entire range of elevation angle $\Phi_B$ of at least 30 degree and less than 90 degree. That is, for the sample of Example 1, if back reflection spectrum measurement was performed in the direction perpendicular to the shearing direction D as the direction of the predetermined azimuth angle $\theta_1$ and in the whole range of elevation angle $\Phi_B$ from the sheet surface of at least 60 degree and less than 90 degree, it was confirmed that the intensity of the Bragg reflection was not zero (0) (Condition (1)). Hence, as explained with reference to FIG. 3C, it is suggested that some of the crystal domains have crystal lattice planes inclined to the sheet surface.

Among elevation angles $\Phi_B$ from the sheet surface in the range of from 60 degree to 90 degree, FIGS. 17A to 17C show the results at typical elevation angles of 60 degree, 70 degree, and 80 degree, respectively. From FIGS. 17A to 17C, it was found that, at any of the elevation angles, the intensity of Bragg reflection in the sample of Example 1 reached a maximum at an azimuth angle θ of 90 degree. Although not illustrated, the same results were obtained at all elevation angles $\Phi_B$ other than the elevation angles of 60 degree, 70 degree, and 80 degree, the elevation angles $\Phi_B$ being measured in the range of from 60 degree to 90 degree. That is, it was confirmed that, in the sample of Example 1, if the back reflection spectrum measurement was performed with respect to the azimuth angle dependency on the sheet surface in the entire range of elevation angle $\Phi_B$ from the sheet surface of at least 60 degree and less than 90 degree, the intensity had the maximum value at the direction perpendicular to the shearing direction D as the direction of the predetermined azimuth angle $\theta_1$ (the above-mentioned Condition (2)). From this, it is suggested that some of the crystal domains are oriented to the direction perpendicular to the direction of the predetermined azimuth dangle $\theta_1$ (shearing direction D).

From FIGS. 18A to 23, it was found that, as in the case of Example 1, all of the samples of Examples 4 to 6 satisfied the above-mentioned Conditions (1) and (2). Although not illustrated, as in the case of Example 1 and Examples 4 to 6, the samples of Examples 2 and 3 also exhibited elevation angle dependence and azimuth angle dependence. Furthermore, also in Examples 7 and 10, when illumination light was irradiated from a direction different from a direction squarely facing the sheet surface and perpendicular to the shearing direction, a blue structural color was developed, and hence, it was suggested that, as in the case of Example 1 and Examples 4 to 6, the samples of Examples 7 and 10 exhibited elevation angle dependence and azimuth angle dependence.

Figure 24A:
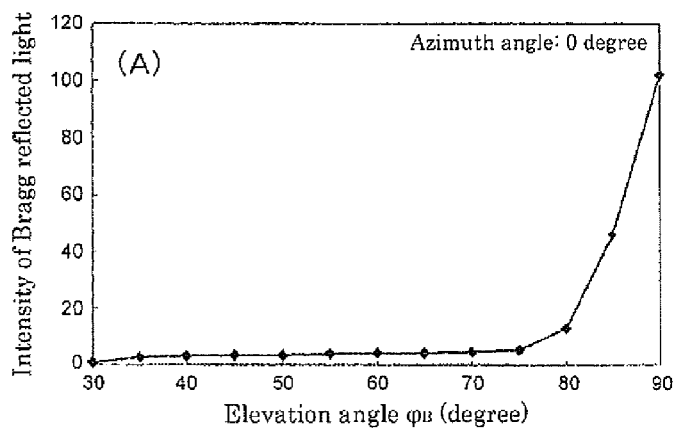
FIG. 24A is a diagram illustrating dependency on the elevation angle of the intensity of Bragg reflection of the sample of Comparative Example 8.
Figure 24B:
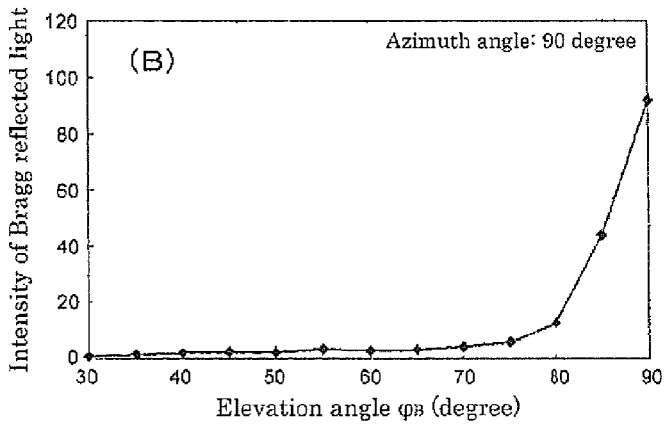
FIG. 24B is a diagram illustrating dependency on the elevation angle of the intensity of Bragg reflection of the sample of Comparative Example 8.
Figure 25:
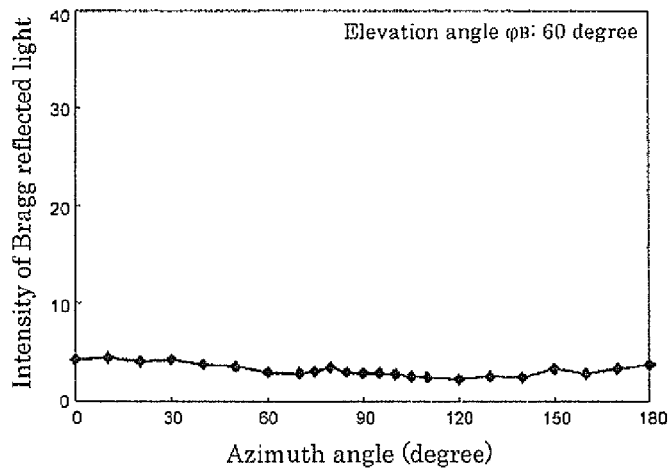
FIG. 25 is a diagram illustrating dependency on the azimuth angle of the intensity of Bragg reflection of the sample of Comparative Example 8.

According to FIGS. 24A and 24B, the sample of Comparative Example 8 satisfied the above-mentioned Condition (1). However, from FIG. 25, it was found that the intensity of Bragg reflection in the sample of Comparative Example 8 was not dependent on azimuth angle at all, and thus, the above-mentioned Condition (2) was not satisfied. Furthermore, according to FIGS. 26A and 26B, in the sample of Comparative Example 9, Bragg reflection did not in neither the shearing direction D nor a direction perpendicular to the shearing direction D if it was other than in the neighborhood of 90 degree, and thus, the above-mentioned Condition (1) was not satisfied. Furthermore, from FIG. 27, it was found that, in the sample of Comparative Example 9, Bragg reflection did not occur at any azimuth angle θ when the elevation angle $\Phi_B$ was 60 degree, and thus, the above-mentioned Condition (2) was not satisfied.

Hence, it was shown that the samples of Examples 1 to 7, and 10 caused Bragg reflection under specific conditions, and therefore, a plurality of crystal domains in which colloidal particles were immobilized in resin were included and the intensity of Bragg reflection caused in such a plurality of crystal domains:

(1) was not zero (0) when measured with respect to the predetermined azimuth angle on the sheet surface and in the range of elevation angle $\Phi_B$ from the sheet surface of the samples of at least 60 degree and less than 90 degree (in the Examples, in the direction perpendicular to the shearing direction D and the azimuth angle θ of 90 or 270 degree); and (2) exhibited the maximum value at the predetermined azimuth angle (in Examples, the direction perpendicular to the shearing direction D and the azimuth angle θ of 90 or 270 degree) if the azimuth angle dependency on the sheet surface was measured in the range of elevation angle $\Phi_B$ from the sheet surface of at least 60 degree and less than 90 degree, such that a plurality crystal domains were oriented.

Furthermore, from the results of Examples 1 to 7, and 10, it was shown that there is no limitation on the kind, flexibility, and hardness of a resin. From the results of Examples 1 to 7, and 10, it was shown that the particle concentration is preferably not less than 2% by volume and not exceeding 35% by volume, more preferably not less than 10% by volume and not exceeding 20% by volume. From the results of Example 5, Example 7, and Comparative Example 9, it was shown that the sheet thickness is preferably more than 0.3 mm and not exceeding 10 mm, more preferably not less than 0.5 mm and not exceeding 5 mm, and still more preferably not less than 0.7 mm and not exceeding 3 mm.

Example 11

In Example 11, using the sample of Example 3, detection of unevenness distribution of a test object was performed. As the test object, a relief plate having a projection portion (820 in FIG. 8) shaped like a handle of a double clip was used. This test object was covered with the sample of Example 3 via the a black rubber sheet as an opaque flexible sheet that is interposed therebetween, and was pressed with a glass plate (610 in FIG. 8) as a hard transparent plate (the step S710 in FIG. 7). Subsequently, the sample of Example 3 was irradiated with fluorescent light as illumination light, and observed through the glass plate (the step S720 in FIG. 7). Specifically, illumination light was irradiated on the sample of Example 3 from a direction (A is 90 degree) perpendicular to the shearing direction for the sample of Example 3 at an elevation angle Φ of 45 degree with respect to the sheet surface of the sample, and a structural color was photographed with a digital camera. Based on images taken by the digital camera as observation results, detection of unevenness distribution of the test object was performed (the step S730 in FIG. 7).

Figure 28A:
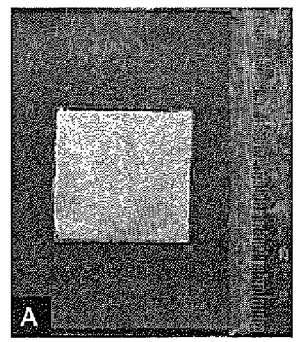
FIG. 28A is a diagram showing a digital-camera image as an observation result of Example 11.
Figure 28B:
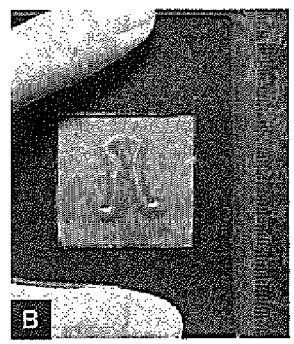
FIG. 28B is a diagram showing a digital-camera image as an observation result of Example 11.

FIGS. 28A and 28B are digital-camera-taken images as the observation results in Example 11. FIG. 28A is a digital-camera-taken image of the sample of Example 3 before the pressing step, and the entirety of the sample assumes a red color. FIG. 28B is a digital-camera-taken image of the sample of Example 3 after the pressing step, and a part of the sample assumes a blue color. These two figures differ in color distribution of structural color, and, in FIG. 28B, there was an area in which a structural color changed from red to blue. It was confirmed that this area corresponded to the convex portion in the shape of a handle of a double clip.

Hence, it was confirmed that the use of the easily deformable sheet of colloidal crystals immobilized in resin according to the present invention allows the unevenness distribution of a test object to be detected. Furthermore, the color distribution of structural color changed according to the unevenness of the test object, and hence, it was found that the method of displaying a structural color according to the present invention, the method being described with reference to FIG. 6, is also effective.

Example 12

In Example 12, using the sample of Example 3, detection of hardness distribution of a test object was performed. The same procedure as that in Example 11 was employed, except that a flexible sponge organization in which cap nuts (two pieces) made of hard metal were embedded was used as the test object.

Figure 29A:
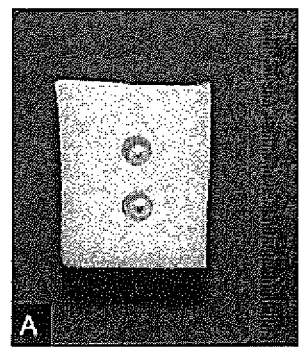
FIG. 29A is a diagram showing a digital-camera image as an observation result of Example 12.
Figure 29B:
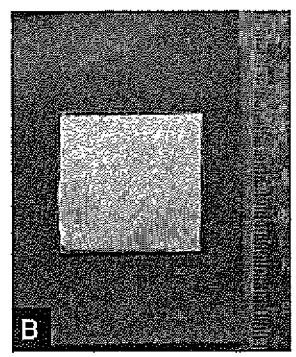
FIG. 29B is a diagram showing a digital-camera image as an observation result of Example 12.
Figure 29C:
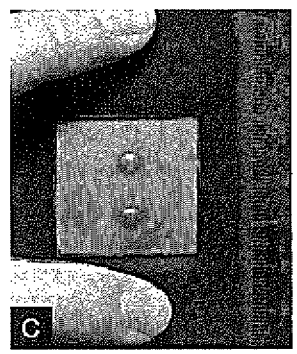
FIG. 29C is a diagram showing a digital-camera image as an observation result of Example 12.

FIGS. 29A to 29C are digital-camera-taken images of the observation results in Example 12. FIG. 29A is a digital-camera-taken image of the test object. FIG. 29B is a digital-camera-taken image of the sample of Example 3 before the pressing step, and the entirety of the sample assumes a red color. FIG. 29C is a digital-camera-taken image of the sample of Example 3 after the pressing step, and a part of the sample assumes a blue color. When FIG. 29B is compared with FIG. 29C, these two figures differ in color distribution of structural color, and, in FIG. 29C, there was an area in which the structural color changed from red to blue. It was confirmed that this area corresponded to an area in which the metal cap nuts illustrated in FIG. 29A are present.

Hence, it was confirmed that the use of the easily deformable sheet of colloidal crystals immobilized in resin according to the present invention makes it possible to detect the hardness distribution of a test object.

INDUSTRIAL APPLICABILITY

The use of the sheet of colloidal crystals immobilized in resin according to the present invention makes it possible for an observer squarely facing the sheet surface to easily observe a structural color by Bragg reflection without overlapping of the observation axis of the observer squarely facing the sheet surface and the illumination axis of illumination light. Furthermore, the use of the sheet of colloidal crystals immobilized in resin according to the present makes it possible for an observer to observe a structural color under a condition where surface reflected light and Bragg reflected light do not overlap, and thus, the effect of clear color development is produced. The sheet of colloidal crystals immobilized in resin according to the present invention functions as a decoration made by making use of the clear color development or a display having various patterns. Furthermore, the use of the sheet of colloidal crystals immobilized in resin according to the present invention makes it possible to detect the unevenness distribution or hardness distribution of a test object by making use of a change in structural color.

In order to distinguish genuine goods from counterfeit goods, a distinguishing tag (what is called a forgery prevention tag) produced using a special material, such as leather, cloth having a special organization, and a luminous material such as a holographic film, is often used for high-grade clothes, bags, and other articles. The sheet of colloidal crystals immobilized in resin according to the present invention has special color development characteristics that conventional materials do not have, the characteristics being such that, for example, a clear structural color can be observed from the squarely facing direction by oblique illumination, and the presence or absence of color development changes according to the azimuth angle of the illumination at that time. Through the utilization of such color development characteristics, the sheet of colloidal crystals immobilized in resin according to the present invention can be also made use of for forgery prevention, for example, by being employed as a material of such forgery prevention tag.

Furthermore, a structural color sheet including the sheet pieces of colloidal crystals immobilized in resin that are cut out of the sheet of colloidal crystals immobilized in resin according to the present invention makes possible the irradiation of illumination light from an arbitrary direction, and therefore, there is no limitation on embodiment, which is advantageous.

EXPLANATION OF NUMERALS 100 sheet of colloidal crystals immobilized in resin
110 crystal domain 120, 920 resin
130 colloidal particle 200 coaxial fiber spectrometer
210 light source 220 spectrometer 230 optical fiber
240 fiber head 250 irradiation light
260 reflected light 400 liquid colloidal dispersion
410, 420 glass plate 500 wall 510 illumination light
520, 630 Bragg reflected light 30 surface reflected light
600 relief plate 610 hard transparent plate
620 pattern 640 color distribution 810 test object
820 convex portion 830 reflected light
840 observation result
850 color distribution before measurement
900 structural color sheet
910 sheet piece of sheet of colloidal crystals immobilized in resin

What is claimed is:
1. A sheet of colloidal crystals immobilized in resin including a plurality of crystal domains, wherein:
the plurality of crystal domains comprise colloidal particles immobilized in resin and the colloidal particles are arranged in a three-dimensional periodic manner configured to form crystal lattice planes inclined to a surface of the sheet of colloidal crystals immobilized in resin to exhibit an effect of Bragg reflection, such that, the plurality of crystal domains comprising the crystal lattice planes are oriented in the sheet of colloidal crystals immobilized in resin while the crystal lattice planes remain inclined to the surface of the sheet of colloidal crystals immobilized in resin such that, in back reflection spectrum measurement to the surface of the sheet of colloidal crystals immobilized in resin, intensity of Bragg reflection caused in the plurality of crystal domains included in the sheet of colloidal crystals immobilized in resin exhibits:
(1) a value sufficient to be recognized beyond measurement errors if measured with respect to a predetermined azimuth angle on the sheet surface and at a plurality of elevation angles from the sheet surface of at least 60° and less than 90°; and (2) an azimuth dependency, such that the intensity of Bragg reflection caused in the plurality of crystal domains exhibits a maximum value at the predetermined azimuth angle wherein the plurality of crystal domains are so oriented that the crystal lattice planes therein are oriented to the predetermined azimuth angle on the sheet surface if measured with respect to a constant elevation angle from the sheet surface, wherein the constant elevation angle is at least 60° and less than 90°.

2. The sheet of colloidal crystals immobilized in resin according to claim 1, wherein:
the sheet is manufactured by applying a shearing treatment and
a direction of the predetermined azimuth angle is perpendicular to a shearing direction in the shearing treatment.

3. The sheet of colloidal crystals immobilized in resin according to claim 1, wherein a particle concentration of the colloidal particles is at least 2% by volume and not exceeding 35% by volume.

4. The sheet of colloidal crystals immobilized in resin according to claim 1, wherein the resin is selected from the group consisting of acrylic resin, epoxy resin, siloxane resin (silicone), urethane resin, polyester resin, alkyd resin, fluorine resin, and polyether resin.

5. The sheet of colloidal crystals immobilized in resin according to claim 4, wherein:
the resin is acrylic resin and
a compound to form the acrylic resin is at least one selected from the group consisting of methyl (meth)acrylate, 2-hydroxyethyl (meth)acrylate, 2-hydroxypropyl (meth)acrylate, 4-hydroxybutyl (meth)acrylate, methoxy triethylene glycol (meth)acrylate, methoxy tetraethylene glycol (meth)acrylate, methoxy polyethylene glycol (meth)acrylate, ethylene di(meth)acrylate, triethylene glycol di(meth)acrylate, tetraethylene glycol di(meth)acrylate, polyethylene glycol di(meth)acrylate, polypropylene glycol di(meth)acrylate, trimethylolpropane tri(meth)acrylate, pentaerythritol tri(meth)acrylate, dipentaerythritol hexa(meth)acrylate, and pentaerythritol tetra(meth)acrylate.

6. The sheet of colloidal crystals immobilized in resin according to claim 4, wherein:
the resin is epoxy resin and
a compound to form the epoxy resin comprises a diglycidyl ester derivative compound and/or a diglycidyl ether derivative compound, and a phthalic anhydride derivative compound.

7. The sheet of colloidal crystals immobilized in resin according to claim 6, wherein the diglycidyl ester derivative compound is phthalic acid diglycidyl ester and/or hexahydrophthalic acid diglycidyl ester.

8. The sheet of colloidal crystals immobilized in resin according to claim 6, wherein the diglycidyl ether derivative compound is at least one selected from the group consisting of glycerol polyglycidyl ether; 1,4-butanediol diglycidyl ether; and bisphenol-A diglycidyl ether.

9. The sheet of colloidal crystals immobilized in resin according to claim 6, wherein the phthalic anhydride derivative compound is 4-methylhexahydrophthalic anhydride and/or hexahydrophthalic anhydride.

10. The sheet of colloidal crystals immobilized in resin according to claim 1, wherein a thickness of the sheet of colloidal crystals immobilized in resin is more than 0.3 mm and not exceeding 10 mm.

11. A method of displaying a structural color based on colloidal crystals comprising the step of:
irradiating a sheet of colloidal crystals immobilized in resin according to claim 1 with illumination light.

12. The method according to claim 11 wherein the step of irradiating the sheet with the illumination light is characterized by irradiating the sheet with the illumination light from a direction different from a squarely facing direction against a sheet surface of the sheet of colloidal crystals immobilized in resin.

13. The method according to claim 11 wherein:
the sheet of colloidal crystals immobilized in resin is manufactured by applying a shearing treatment; and
the step of irradiating the sheet with the illumination light is characterized by irradiating the sheet with the illumination light from a direction perpendicular to a shearing direction of the shearing treatment.

14. The method according to claim 11 wherein the sheet of colloidal crystals immobilized in resin has a pattern comprising a character or a figure.

15. A method of displaying a structural color based on colloidal crystals comprising the steps of:
irradiating a sheet of colloidal crystals immobilized in resin according to claim 1 with illumination light and
pressing the sheet of colloidal crystals immobilized in resin with a hard transparent plate prior to the step of irradiating the sheet with the illumination light wherein the sheet of colloidal crystals immobilized in resin is sandwiched at least between the hard transparent plate and a relief plate in which a pattern comprising a character or a figure is formed with a convex and/or a concave.

16. A method of detecting an unevenness distribution or a hardness distribution of a test object comprises the steps of:
covering the test object with a sheet of colloidal crystals immobilized in resin according to claim 1 and pressing the sheet with a hard transparent plate;
irradiating the sheet of colloidal crystals immobilized in resin with illumination light and observing the sheet of colloidal crystals immobilized in resin through the hard transparent plate; and
detecting an unevenness distribution or a hardness distribution based on an observation result obtained in the step of observation.

17. The method according to claim 16 wherein the step of observation comprises irradiating the sheet with the illumination light from a direction different from a squarely facing direction against a sheet surface of the sheet of colloidal crystals immobilized in resin and observing the sheet.

18. The method according to claim 16 wherein the step of detection comprises:
detecting that the test object does not have the unevenness distribution or the hardness distribution when the observation result is same as that of the sheet of colloidal crystals immobilized in resin prior to the step of pressing; and
detecting that the test object has the unevenness distribution or the hardness distribution when the observation result is different from that of the sheet of colloidal crystals immobilized in resin prior to the step of pressing.

19. A structural color sheet in which a plurality of sheet pieces of colloidal crystals immobilized in resin are immobilized in resin;

wherein the plurality of sheet pieces of colloidal crystals immobilized in resin are cut out of a sheet of colloidal crystals immobilized in resin according to claim 1, and wherein the plurality of sheet pieces of colloidal crystals immobilized in resin are arranged in an arbitrary orientation relationship in the resin.

20. The sheet of colloidal crystals immobilized in resin according to claim 10, wherein a thickness of the sheet of colloidal crystals immobilized in resin is more than 0.7 mm and not exceeding 5 mm.

* * * * *